(12) United States Patent
Humljan et al.

(10) Patent No.: US 9,212,118 B2
(45) Date of Patent: Dec. 15, 2015

(54) SYNTHESIS OF INTERMEDIATES FOR PREPARING ANACETRAPIB AND DERIVATIVES THEREOF

(75) Inventors: Jan Humljan, Ljubljana (SI); Nenad Maras, Ljubljana (SI)

(73) Assignee: LEK PHARMACEUTICALS D.D., Ljubljana (SI)

( * ) Notice: Subject to any disclaimer, the term of this patent is extended or adjusted under 35 U.S.C. 154(b) by 24 days.

(21) Appl. No.: 13/996,955

(22) PCT Filed: Dec. 21, 2011

(86) PCT No.: PCT/EP2011/073660
§ 371 (c)(1),
(2), (4) Date: Jan. 29, 2014

(87) PCT Pub. No.: WO2012/085133
PCT Pub. Date: Jun. 28, 2012

(65) Prior Publication Data
US 2014/0135368 A1    May 15, 2014

(30) Foreign Application Priority Data

Dec. 23, 2010  (EP) .................................... 10016010

(51) Int. Cl.
| C07C 41/24 | (2006.01) |
| C07C 41/18 | (2006.01) |
| C07C 41/30 | (2006.01) |
| C07C 41/26 | (2006.01) |
| C07C 45/68 | (2006.01) |
| C07D 263/22 | (2006.01) |
| C07C 253/30 | (2006.01) |
| A61K 31/421 | (2006.01) |
| C07C 41/22 | (2006.01) |
| C07C 43/225 | (2006.01) |
| C07D 263/20 | (2006.01) |

(52) U.S. Cl.
CPC ................ *C07C 41/26* (2013.01); *A61K 31/421* (2013.01); *C07C 41/18* (2013.01); *C07C 41/22* (2013.01); *C07C 41/30* (2013.01); *C07C 43/225* (2013.01); *C07C 45/68* (2013.01); *C07C 253/30* (2013.01); *C07D 263/20* (2013.01); *C07D 263/22* (2013.01)

(58) Field of Classification Search
CPC .......... C07C 41/24; C07C 41/18; C07C 41/30
See application file for complete search history.

(56) References Cited

FOREIGN PATENT DOCUMENTS

| WO | WO 2006/014357 A1 | 2/2006 |
| WO | WO 2006/014357 A1 | 2/2006 |
| WO | WO 2007/005572 A1 | 1/2007 |
| WO | WO 2007/005572 A1 | 1/2007 |
| WO | WO 2007/041494 A2 | 4/2007 |
| WO | WO 2008/115442 A1 | 9/2008 |

*Primary Examiner* — Shawquia Jackson
(74) *Attorney, Agent, or Firm* — Arent Fox LLP

(57) ABSTRACT

The present invention relates to the field of organic chemistry, more specifically to the synthesis of intermediate compounds which can be used in the synthesis of pharmaceutically active agents such as anacetrapib or derivatives thereof.

14 Claims, No Drawings

SYNTHESIS OF INTERMEDIATES FOR PREPARING ANACETRAPIB AND DERIVATIVES THEREOF

CROSS-REFERENCE TO RELATED APPLICATION

This application is a National Stage entry of International Application No. PCT/EP2011/073660, filed Dec. 21, 2011, which claims priority to European Application No. 10016010.0, filed Dec. 23, 2010, the entire specifications, claims and drawings of which are incorporated herewith by reference.

FIELD OF THE INVENTION

The present invention relates to the field of organic chemistry, more specifically to the synthesis of intermediate compounds which can be used in the synthesis of pharmaceutically active agents such as anacetrapib or derivatives thereof.

BACKGROUND OF THE INVENTION

Anacetrapib (chemically named (4S,5R)-5-[3,5-bis(trifluoromethyl)phenyl]-3-[[2-(4-fluoro-2-methoxy-5-propan-2-ylphenyl)-5-(trifluoromethyl)phenyl]methyl]-4-methyl-1,3-oxazolidin-2-one) having the structural formula

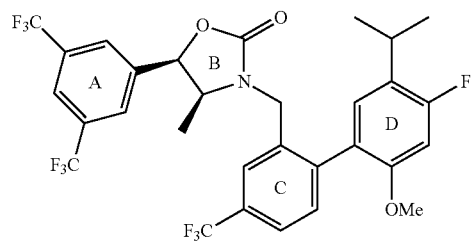

has been shown to act as an inhibitor of cholesteryl ester transfer protein (CETP). The complex molecular structure of anacetrapib comprises four cycles A, B, C and D as shown above, wherein this structure can be built up in various manners. The following linear (A+B+C+D) and convergent approach (AB+CD) for the synthesis of anacetrapib have been disclosed in patent applications WO 2006/014413 and WO 2007/005572, respectively. In the preferred embodiments of both aforementioned approaches, the compounds shown in Scheme 1 wherefrom cycle moieties C and D derive, are used as the starting material Scheme 1

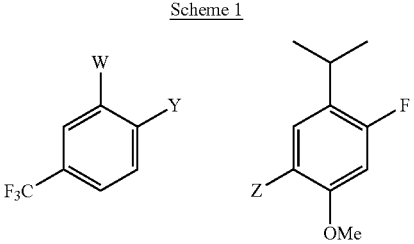

wherein substituents Y and Z represent groups suitable for biaryl coupling, and W is a group which is $CH_2Q$ or a group which can be converted to $CH_2Q$, in which Q is halo, hydroxy, substituted hydroxy, amino or substituted amino for the direct coupling to another molecule such as a multicycle molecule comprising cycles A and B.

In WO 2006/014413 and WO 2007/005572, 1-halo-4-fluoro-5-isopropyl-2-methoxybenzene as shown in Scheme 2 (XMIP, wherein X is bromo or iodo) is used as the common key intermediate for coupling of fragment D.

Scheme 2

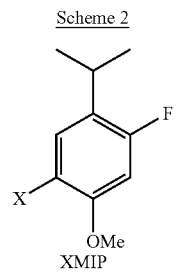

XMIP

The convergent synthesis described in WO 2007/005572 in which biaryl derivative is prepared from 1-(2-fluoro-4-methoxyphenyl)ethanone (compound 1 in Scheme 3) requires a three-step process to obtain 1-bromo-4-fluoro-5-isopropyl-2-methoxybenzene (compound 5 in Scheme 3) as show in Scheme 3 and appears to be the most favorable approach.

Scheme 3

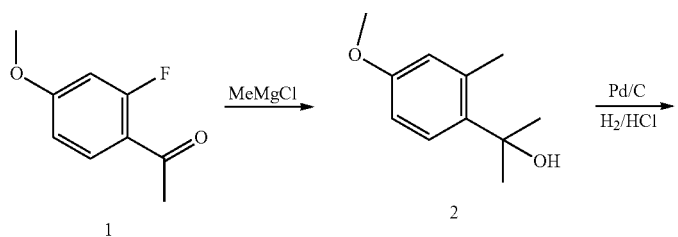

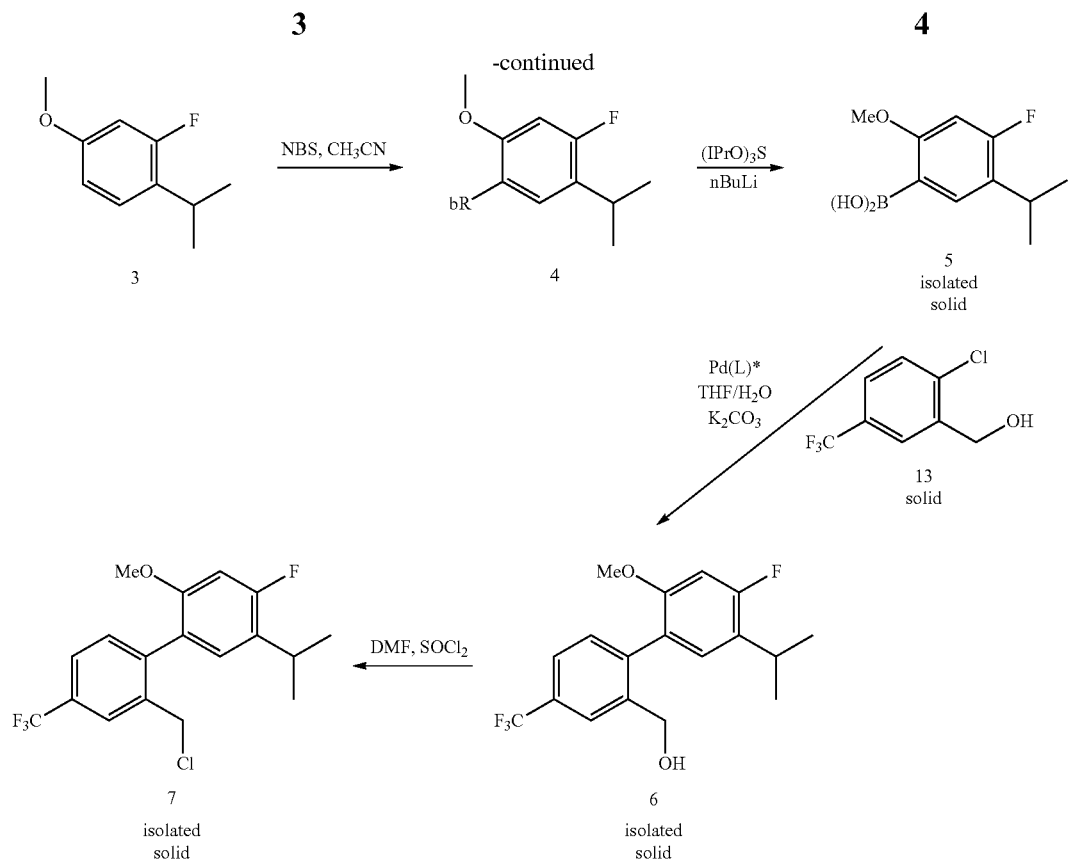

However, the methods described in the aforementioned patent applications have some drawbacks regarding impurity profile, yields and the use of genotoxic solvents. It has been surprisingly found that the method described in WO 2007/005572 leads to an impure final product, which is hard to purify to a pharmaceutical grade by conventional purification methods. Our careful analysis discovered an impurity desmethylanacetrapib (DMAP), a compound having the structural formula

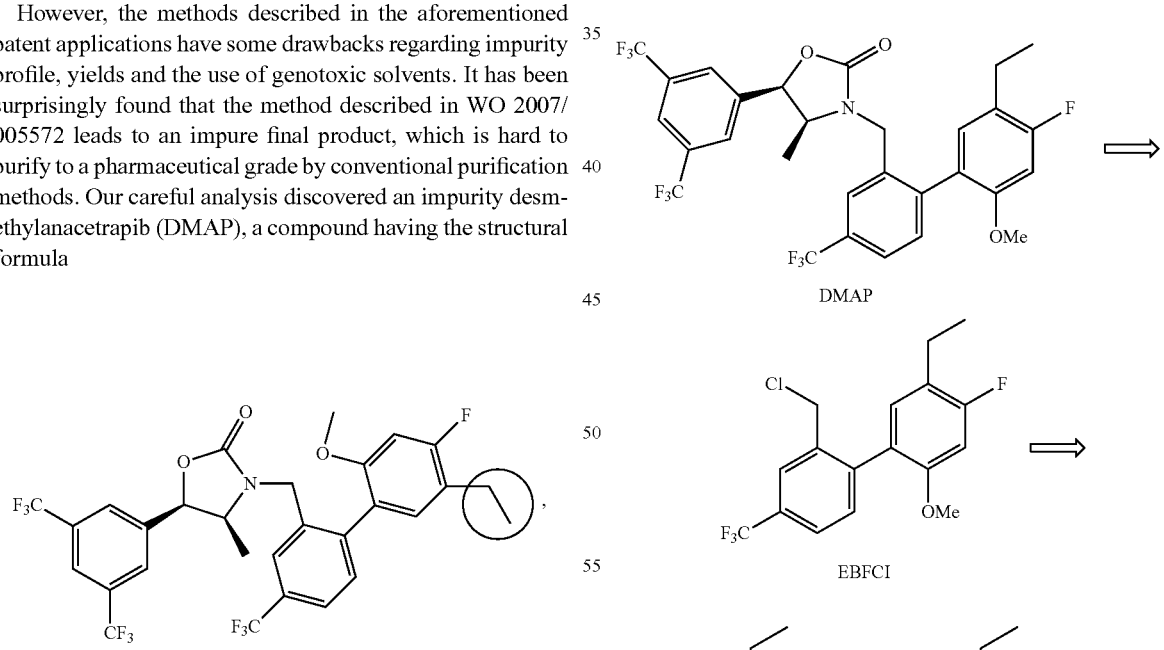

wherein DMAP differs from anacetrapib in that cycle D is substituted with an ethyl moiety (indicated with a circle) instead of an isopropyl moiety.

As shown in Scheme 4, desmethylanacetrapib (DMAP) originates from a very early step of the synthesis described in WO 2007/005572.

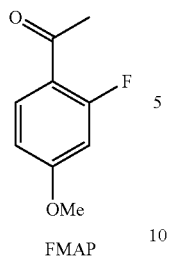

FMAP wherein 1-ethyl-2-fluoro-4-methoxybenzene (MET) is a result of incompleteness of Grignard methylation of 1-(2-fluoro-4-methoxyphenyl)ethanone (FMAP) due to enolization with the Grignard reagent of the acetophenone FMAP from which the remaining starting material 1-(2-fluoro-4-methoxyphenyl)ethanone (FMAP) is recovered after isolation which is then converted to 1-ethyl-2-fluoro-4-methoxybenzene (MET) in the consecutive step (Scheme 5). Furthermore, when reproducing the prior art process it was observed that approximately 5-10% of FMAP remains in the reaction process and that the impurity MET formed can not be removed in the following steps. Moreover, MET is first transformed to 1-bromo-5-ethyl-4-fluoro-2-methoxybenzene (BrMET) and then to chloro biaryl impurity 2'-(chloromethyl)-5-ethyl-4-fluoro-2-methoxy-4'-(trifluoromethyl)biphenyl (EBFCI) in the consecutive steps, which after coupling with heterocyclic intermediate results in the additional impurity desmethylanacetrapib (DMAP) in the final product anacetrapib.

Scheme 5

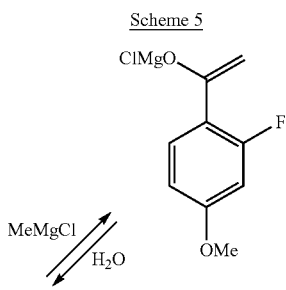

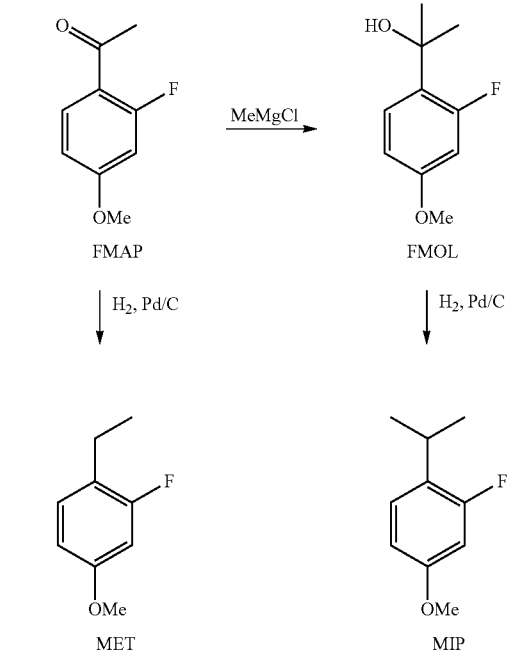

In order to overcome the above described problem, it was suggested to use anhydrous cerium (III) chloride, which is highly hydroscopic and thus not feasible and/or economical for the usage in industrial scale. Furthermore, while repeating this process, the reaction is too slow and not complete.

Another synthesis described in WO 2007/136672 starts from 1-bromo-2,4-difluorobenzene (compound 1 in Scheme 6) and requires a four-step process to obtain 1-bromo-4-fluoro-5-isopropyl-2-methoxybenzene (compound 5 in Scheme 6) as shown in Scheme 6.

Scheme 6

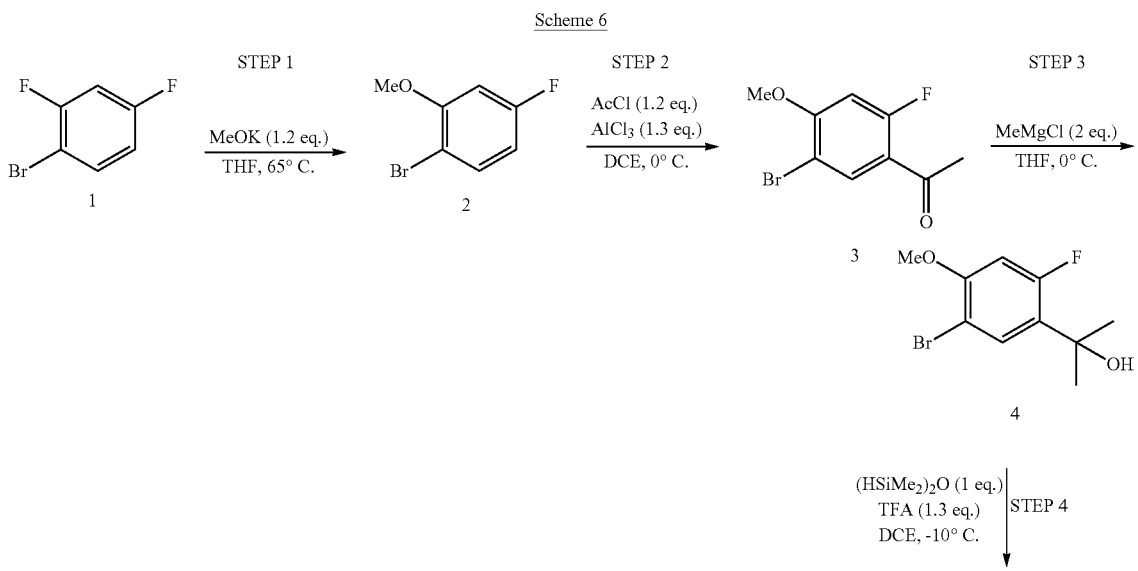

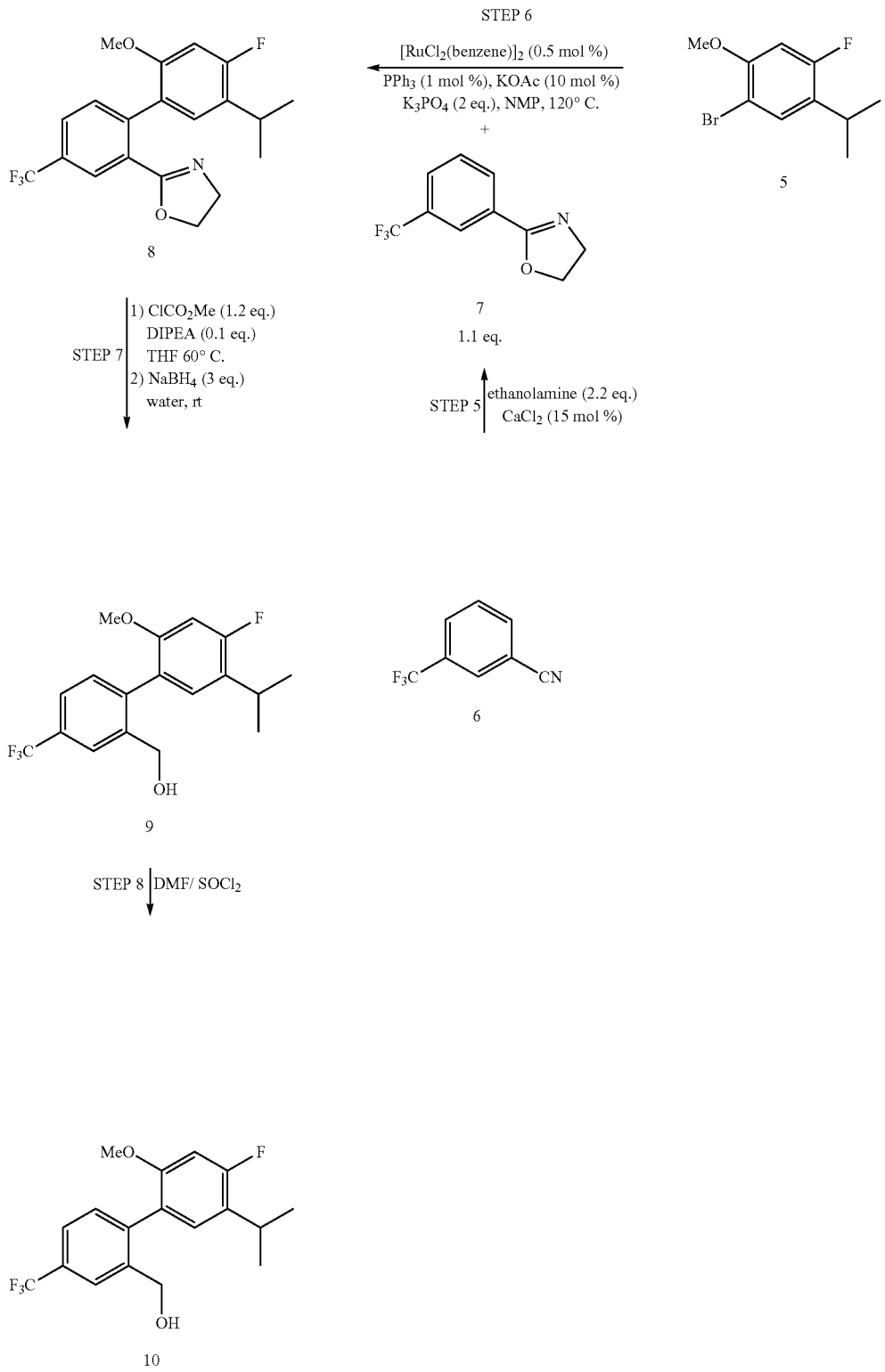

The critical step of grignardation is performed on the corresponding bromo derivative, what can have some advantages in view of desmethyl impurities. However, the propanolderivative BrFMOL (compound 4 in Scheme 6) cannot be simply hydrogenated to isopropyl derivative BrMIP (compound 5 in Scheme 6) due to considerable debromination to MIP (Scheme 7).

Scheme 7

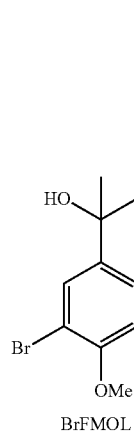

BrFMOL

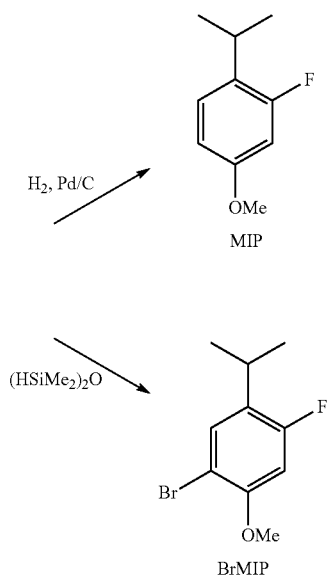

MIP

BrMIP

Consequently, said conversion should be performed using tetramethyldisiloxane (TMDSO), which is less suitable reagent for industrial use. Additionally, applying TMDSO leads to modest yields and the formation of siloxane impurities that are difficult to remove. Further drawbacks of the whole synthetic scheme of WO 2007/136672 are the use of dichloroethane as a solvent, since dichloroethane is reasonably anticipated to be human carcinogen, and the use of uneconomical ruthenium catalysts.

Therefore, there is an unmet need for a preparation of highly pure intermediates for the synthesis of cholesterylester transfer protein (CETP) inhibitors such as anacetrapib.

SUMMARY OF THE INVENTION

Various aspects, advantageous features and preferred embodiments of the present invention as summarized in the following items, respectively alone and in combination, contribute to solving the object of the invention.
(1) A process for preparing a compound of formula II

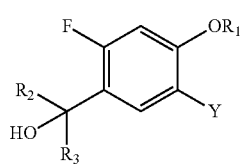

wherein R1, R2 and R3 are independently from each other selected from substituted or unsubstituted C1-C6 alkyl, and Y is Br, Cl, I or H, which process comprises treating a compound of formula I

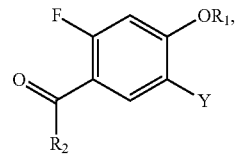

wherein $R_1$, $R_2$ and Y are defined as above,
with a Grignard reagent in a first solvent, in the presence of a second solvent inert to Grignard reagents selected from the group consisting of $C_1$-$C_6$ haloalkanes, substituted or unsubstituted $C_6$-aromatics and dialkyloxyethanes comprising $C_1$-$C_6$ alkyl moiety/moieties.

The term "alkyl" as used herein means straight or branched chain alkyl moiety.

The term "substituted $C_6$-aromatics" as used herein means benzene substituted with at least one substituent selected from the group consisting of $C_1$-$C_3$ alkyl, $C_1$-$C_3$ alkoxy and halogen. Preferably, substituted benzene is toluene, anisole or xylene.

The term "Grignard reagent" as used herein means an organometallic compound in form of Alkyl-M-Hal, wherein M denotes a metal and Hal denotes halogen, preferably the organometallic compound is alkyl-magnesium halide. The Grignard reagent may either be provided in form of a commercial ready to use Grignard solution, that is a solution wherein the Grignard reagent is dissolved in a suitable solvent, or a selfmade Grignard reagent which is obtained by reaction of elemental magnesium with alkyl halide in a suitable solvent.

The term "first solvent" as used herein means a solvent wherein Grignard reagent is typically reacted with another compound, that is the solvent wherein commercial ready-to-use Grignard is dissolved or the solvent wherein selfmade Grignard reagent is prepared.

The term "second solvent" as used herein means a solvent which is different from the first solvent.

The procedural concept according to this aspect of the invention provides for a compound of formula II representing a highly valuable intermediate for the preparation of pharmaceutically active agents such as anacetrapib or derivatives thereof, since compound of formula II has a high purity owing to the simple and efficient Grignard reaction wherein chemoselectivity (addition versus enolization) is significantly increased, which in turn provides for a product in form of compound of formula II being essentially free of starting material of compound of formula I. Hence, subsequent purification of compound of formula II from compound of formula I is not only significantly facilitated and avoids further laborious purification step(s), but it also encounters the problem that it is very difficult to remove compound of formula I completely from compound of formula II. If on the other hand following conventional Grignard approach, considerable amounts of at least about 5% of compound of formula I will stay in the reaction product. Thus, in subsequent reaction steps, a compound prepared with the present Grignard reaction provides for significantly reduced amounts of impurities, in particular "desalkyl" impurities as elucidated under items (50) to (53) below.
(2) The process according to any one of item (1), wherein the reaction is carried out in a mixture of a first solvent and a second solvent, wherein the second solvent is inert to Grignard reagents, and is selected from the group consisting of $C_1$-$C_6$ haloalkanes, substituted or unsubstituted $C_6$-aromatics and dialkyloxyethanes comprising $C_1$-$C_6$ alkyl moiety/moieties, and more preferably from the group consisting of dichloromethane (DCM), toluene and 1,2-dimethoxyethane (DME).

As to the meaning of the terms "first solvent" and "second solvent", reference is made to item (1) above.

According to this preferred embodiment, chemoselectivity of the Grignard reaction can be efficiently increased wherein the amount of starting material of compound of formula I in the desired product of compound of formula II is significantly reduced as elucidated in the explanations under item (1) above.

(3) The process according to any one of the preceding items, wherein in compound of formula I (and II), $R_1$ and $R_3$ are independently from each other selected from substituted or unsubstituted $C_1$-$C_6$ alkyl and wherein $R_2$ is substituted or unsubstituted $C_1$-$C_6$ alkyl wherein $C_1$ has at least one hydrogen, and Y is Br or H, preferably $R_1$, $R_2$ (and $R_3$) are methyl (Me) and Y is H.

(4) The process according to any one of the preceding items, wherein the Grignard reagent is $R_3MgX$ wherein $R_3$ is $C_1$-$C_6$ alkyl and X is Cl, Br or I, preferably $R_3MgX$ wherein $R_3$ is $C_1$-$C_6$ alkyl and X is Cl, more preferably MeMgCl.

(5) The process according to any one of items (1) to (4), wherein the first solvent is an ether comprising $C_1$-$C_6$ alkyl moiety/moieties and/or phenyl moiety, preferably the first solvent is selected from the group consisting of diethyl ether, dibutyl ether, methyl tert-butyl ether, anisole, tetrahydrofuran (THF), 1,4-dioxane, more preferably from the group consisting of diethyl ether, methyl tert-butyl ether, THF, 1,4-dioxane, even more preferably THF.

(6) The process according to any one of the preceding items, wherein the second solvent is toluene.

(7) The process according to any one of the preceding items, wherein a first mixture comprising compound of formula I and the second solvent is added to a second mixture comprising Grignard reagent and the first solvent, preferably addition is dropwise.

(8) The process according to any one of the preceding items, wherein the Grignard reagent is used in an amount of 1.0 to 2.0 equivalent(s) relative to compound of formula I, preferably 1.2 to 1.6 equivalent(s).

(9) The process according to any one of the preceding items, wherein treatment with Grignard reagent is carried out at a temperature below 30° C., preferably below 5° C., more preferably below 0° C.

(10) The process according to any one of the preceding items, wherein a volume ratio of first solvent to second solvent is 0.1/1 to 5/1, preferably 0.2/1 to 0.7/1.

(11) The process according to any one of the preceding items, wherein the obtained compound of formula II comprises an impurity in form of unconverted starting material of compound of formula I in an amount of less than 0.50% by weight relative to the total amount of compound of formula II, preferably less than 0.25%, and more preferably less than 0.15%.

(12) The process according to any one of the preceding items, wherein compound of formula II

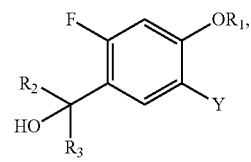

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Y is Br, Cl, I or H, is converted to a compound of formula IV

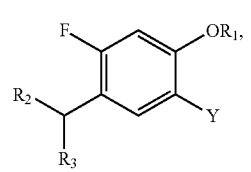

wherein $R_1$, $R_2$, $R_3$ and Y are defined as above, by hydrogenation in the presence of a hydrogenation catalyst.

The term "hydrogenation" as used herein means a reduction reaction wherein hydrogen is the reducing agent.

The term "hydrogenation catalyst" as used herein means a compound or complex capable of catalyzing a hydrogenation reaction.

(13) The process according to item (12), wherein it is further provided for simultaneous hydrogenation of a byproduct in form of compound of formula $III_1$

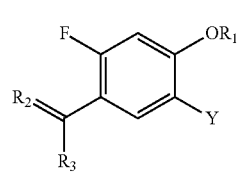

and/or compound of formula $III_2$

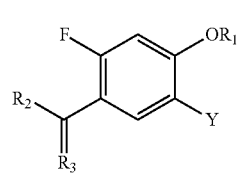

wherein $R_1$ is substituted or unsubstituted $C_1$-$C_6$ alkyl, $R_2$ and $R_3$ are independently from each other selected from substituted or unsubstituted $C_1$-$C_6$ alkyl and alkylidene, and Y is Br, Cl, I or H.

(14) The process according to items (12) or (13), wherein a compound of formula IV'

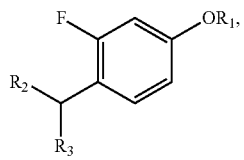

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom,
is converted to a compound of formula VI

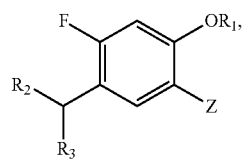

wherein $R_1$, $R_2$ and $R_3$ are defined as above and Z is Br, Cl or I,
by treating compound of formula IV' with a halogenating agent.

The term "halogenating agent" as used herein means a compound capable of substituting hydrogen atom of an aromatic ring system by halogen atom.

Compound of formula IV' is a compound deriving from compound of formula I' wherein Y=H. Compound of formula I' is the preferred starting material in a process according to the preceding items in case a hydrogenation step such as e.g. defined in item (12) or (14) is carried out in a subsequent step, because a starting material of formula I wherein Y=Br, Cl or I, in particular Br, may bear the problem of dehalogenation as elucidated in Scheme 7 above. Thus, if hydrogenation of compound of formula II is intended, the special embodiments of item (14) and (15) provide for introduction of halogen Z subsequent to a hydrogenation or in a one-pot reaction respectively, wherein halogen Z enables further reaction steps such as direct coupling with another suitable compound as defined in any one of items (41) to (48), or conversion to a Grignard reagent as defined in any one of items (28) to (30) or a boronic acid derivative as defined in any one of items (31) to (40) before coupling reactions as defined in items (41) or (42) are carried out.

(15) A process for preparing compound of formula VI

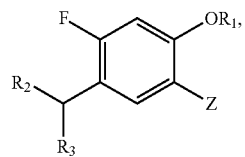

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Z is Br, Cl or I,
by hydrogenating a compound of formula II'

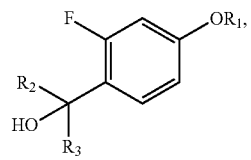

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom; and optionally comprising compound of formula $III_1$'

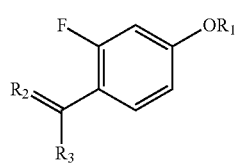

and/or a compound of formula $III_2$'

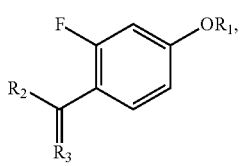

wherein $R_1$, $R_2$ and $R_3$ are defined as above,
in the presence of hydrogen and a hydrogenation catalyst and subsequently by treating the reaction mixture with a halogenating agent
in a one-pot reaction process.

The term "one-pot process/reaction" as used herein means that at least two reactions are subsequently carried out without isolating intermediate compounds.

(16) The process according to item (15), wherein said one pot reaction follows subsequent to a process as defined in any one of items (1) to (12).

(17) The process according to any one of items (13) to (16), wherein compounds of formula $III_1$/$III_2$ and $III_1$'/$III_2$' respectively are present in an amount of at least 30% by weight relative to the total amount of starting material II or II', preferably at least 40% by weight, more preferably at least 50% by weight.

(18) The process according to any one of items (15) to (17), wherein the hydrogenation catalyst is removed from the reaction mixture before treatment with a halogenating agent, preferably catalyst is removed by filtration.

(19) The process according to any one of items (12) to (18), wherein hydrogenation is carried out in $C_1$-$C_6$ alcohols or $C_1$-$C_6$ alkyl esters of $C_1$-$C_6$ carboxylic acids as the solvent, preferably $C_1$-$C_3$ alcohols or $C_1$-$C_3$ alkyl esters of $C_1$-$C_3$ carboxylic acids, more preferably the solvent is selected from the group consisting of methanol, ethanol, isopropyl alcohol, ethyl acetate, isopropyl acetate and acetic acid, even more preferably the solvent is methanol.

(20) The process according to any one of items (12) to (19), wherein hydrogenation is carried out using a hydrogenation catalyst selected from the group consisting of palladium-, platinum- or nickel-catalyst, preferably palladium catalyst, more preferably palladium supported on a solid, even more preferably palladium on activated charcoal.

(21) The process according to any one of items (14) to (20), using halogenating agents, preferably a N-halo substituted compounds, more preferably 1,3-dibromo-5,5-dimethyl-hydantoin (DBDMH).

(22) A process for preparing a compound of formula II

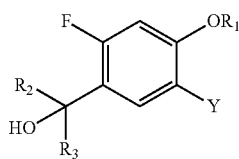

wherein $R_1$ and $R_3$ are independently from each other selected from substituted or unsubstituted $C_1$-$C_6$ alkyl and wherein $R_2$ is substituted or unsubstituted $C_1$-$C_6$ alkyl wherein $C_1$ has at least one hydrogen atom, and Y is Br, Cl, I or H, which process comprises treating a compound of formula I

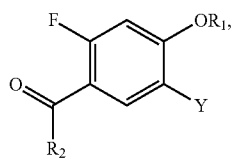

wherein $R_1$, $R_2$ and Y are defined as above, with a Grignard reagent, wherein the reaction mixture is quenched with an organic solvent selected from the group consisting of chloroform or $C_1$-$C_6$ alcohols, preferably methanol.

The term "quenching" as used herein means decomposing a reactive species in order to stop a reaction and to convert intermediate products to stable materials which can be isolated or removed without danger. The solvent(s) used for quenching substantially decrease(s) the formation of dehydrated byproducts.

As to the meaning of the terms "alkyl", "substituted" and "Grignard reagent", reference is made to the explanations under item (1) above.

(23) The process according to any one of item (22), wherein subsequent to quenching with an organic solvent, water or aqueous inorganic acid is added, preferably aqueous HCl is added.

(24) The process according to item (23), wherein the organic solvent and/or water/aqueous inorganic acid is added dropwise, preferably organic solvent and water/aqueous HCl are subsequently added dropwise.

(25) The process according to any one of items (22) to (24), wherein quenching is carried out such that the temperature of the reaction mixture is kept below 30° C.

(26) The process according to any one of items (22) to (25), wherein the obtained compound of formula II comprises a byproduct formed during quenching in form of compound of formula $III_1$

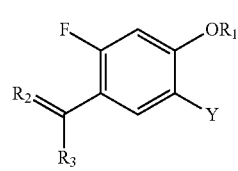

and/or of compound of formula $III_2$

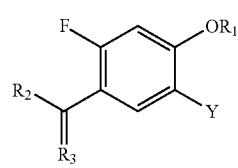

wherein $R_1$ is substituted or unsubstituted $C_1$-$C_6$ alkyl, $R_2$ and $R_3$ are independently from each other selected from substituted or unsubstituted $C_1$-$C_6$ alkyl and alkylidene, and Y is Br, Cl, I or H.

According to this beneficial aspect of the invention, an alternative process for preparing compounds of formula II having high purity is provided. Owing to this alternative process, formation of dehydrated byproducts in form of compound of formula $III_1$ or $III_2$ as defined e.g. in item (26) is effectively prevented. Therefore, it can be dispensed with a laborious subsequent purification, here of compound of formula II, from compound of formula $III_1$ or $III_2$.

(27) The process according to items (22) to (26), wherein in subsequent reaction steps, a compound prepared with the present Grignard reaction provides for significantly reduced amounts of impurities deriving from compound of formula $III_1$ or $III_2$.

The amount of the compound $III_1$ or $III_2$ according to item (26) is less than 2.0% by weight, preferably less than 1.0%, and more preferably less than 0.5%.

(28) The process according to any one of items (12) to (21), wherein compound of formula IV or compound of formula VI

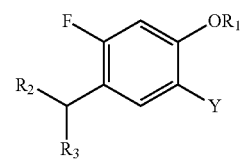

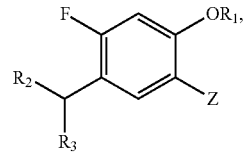

wherein R$_1$ and R$_3$ are independently from each other selected from substituted or unsubstituted C$_1$-C$_6$ alkyl and R$_2$ is substituted or unsubstituted C$_1$-C$_6$ alkyl wherein C$_1$ has at least one hydrogen atom, and Y is H, Cl, Br or I and Z is Cl, Br or I, is treated with magnesium or zinc, or first with butyllithium, Grignard reagent, magnesium or lithium and followed by ZnX$_2$, wherein X is defined as above.

to form a compound of formula VIII

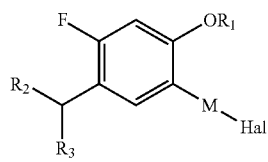

VIII wherein R$_1$, R$_2$ and R$_3$ are defined as above, M is magnesium (Mg) or zinc (Zn), wherein Hal is Cl, Br or I.

(29) The process according to item (28), wherein conversion is carried out at a temperature below 100° C., preferably below 50° C.

(30) The process according to item (28) or (29), wherein in compound of formula VIII M is Mg and Z is Br.

(31) The process according to any one of items (28) to (30), wherein compound of formula VIII is treated with trialkyl borate in order to convert compound of formula VIII to a compound of formula IX

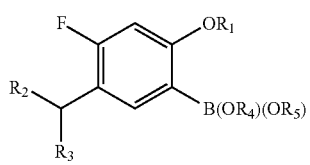

IX wherein R$_1$ and R$_3$ are independently from each other selected from substituted or unsubstituted C$_1$-C$_6$ alkyl and R$_2$ is substituted or unsubstituted C$_1$-C$_6$ alkyl wherein C$_1$ has at least one hydrogen atom, and R$_4$ and R$_5$ are selected from H or substituted or unsubstituted C$_1$-C$_6$ alkyl, or R$_4$ and R$_5$ together form a C$_2$-C$_4$ alkylene, preferably R$_4$ and R$_5$ is H.

(32) The process according to item (31), wherein conversion is carried out in an aprotic solvent or mixture of aprotic solvents, preferably toluene.

(33) The process according to item (31) or (32), wherein conversion is carried out at a temperature above −10° C., preferably above 0° C.

(34) The process according to items (28) to (33), wherein conversion of compound of formula IV or compound of formula VI to compound of formula IX is carried out in a one-pot reaction.

(35) The process according to items (28) to (34), wherein the compound of formula VIII is subjected to further synthesis steps to yield anacetrapib.

(36) The process according to any of items (12) to (21), wherein compound of formula IV or compound of formula VI

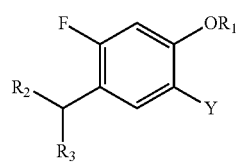

IV''

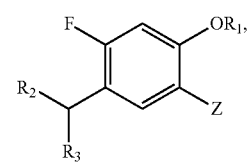

VI wherein R$_1$ and R$_3$ are independently from each other selected from substituted or unsubstituted C$_1$-C$_6$ alkyl and R$_2$ is substituted or unsubstituted C$_1$-C$_6$ alkyl wherein C$_1$ has at least one hydrogen atom, and Y is H, Cl, Br or I and Z is Cl, Br or I, is converted to compound of formula IX

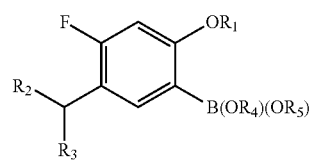

IX wherein R$_1$, R$_2$ and R$_3$ are defined as above and R$_4$ and R$_5$ are selected from H or substituted or unsubstituted C$_1$-C$_6$ alkyl, or R$_4$ and R$_5$ together form a C$_2$-C$_4$ alkylene, by treating compound of formula VI with a trialkyl borate in the presence of organolithium or lithium.

(37) The process according to item (36), wherein the organolithium compound is butyllithium.

(38) The process according to item (37), wherein lithium in C$_5$-C$_7$-alkane is used.

(39) The process according to any one of items (36) to (38), wherein conversion is carried out in an inert aprotic solvent or mixture of solvents, preferably the inert aprotic solvent is an ether comprising aliphatic C$_1$-C$_6$ alkyl moiety/moieties and/or phenyl moiety, preferably the ether is selected from the group consisting of diethyl ether, dibutyl ether, methyl tert-butyl ether, anisole, tetrahydrofuran (THF), 1,4-dioxane, more preferably from the group consisting of diethyl ether, methyl tert-butyl ether, THF, 1,4-dioxane, even more preferably THF.

(40) The process according to item (31) or (36) to (39), wherein trialkyl borate is trimethyl borate or triisopropyl borate.

(41) The process according to any one of items (31) to (40), wherein compound of formula IX'

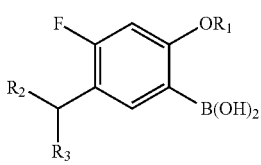

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, is coupled with a compound of formula XI,

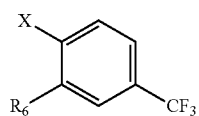

wherein X is selected from Cl, Br, I, —O—$SO_2CF_3$ (—OTf), —$N_2^+$ or —$N(CH_3)_3^+$, preferably X is selected from Cl, Br, I or —OTf, and $R_6$ is $CH_2Q$ or a group which can be converted to $CH_2Q$ group, wherein Q represents a leaving group or a group convertible to a leaving group, preferably Q is selected from the group consisting of halogen, hydroxy, acyl or sulfonyl substituted hydroxy, amino, acyl or sulfonyl substituted amino, more preferably $R_6$ is selected from the group consisting of hydroxymethyl, alkoxymethyl, halogenmethyl wherein halogen is Cl, Br or I, carboxy, alkoxycarbonyl, amidocarbonyl, cyano, formyl, 2-(4,5-dihydro-1,3-oxazolyl) and nitro, to form a compound of formula XII,

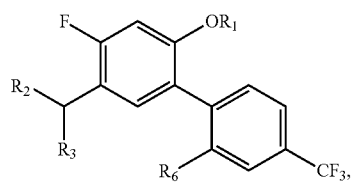

wherein $R_1$, $R_2$, $R_3$ and $R_6$ are defined as above, in the presence of a coupling catalyst.

The terms "leaving group" and "a group convertible to a leaving group" used herein mean a group which is easily substituted by nucleophile substitution reaction. A "group convertible to a leaving group" has the capability of being conventionally converted to a desired leaving group. Optionally the respective leaving group of a precursor group thereof is protected by usual and known protection groups. The respective meanings of these terms become further apparent from the more specific definitions provided herein in the disclosure of preferred embodiments.

The term "alkoxy" as used herein means —O-alkyl, wherein alkyl is straight or branched chain and comprises 1 to 6 carbon atoms, preferably 1 to 4 carbon atoms.

The term "halogen" as used herein means the group consisting of chloro, bromo and iodo.

The term "acyl or sulfonyl substituted hydroxy" as used herein means a carboxylic acid ester —O—C(O)—$R_4$ and a sulfonic acid ester —O—$SO_2$—$R_4$ moiety respectively, wherein $R_4$ is $C_1$-$C_{20}$-alkanoic, substituted or unsubstituted $C_1$-$C_{20}$ alkyl or $C_5$-$C_{20}$ aryl, preferably substituted or unsubstituted $C_1$-$C_{10}$ alkyl or $C_6$-$C_{12}$ aryl and substituted or unsubstituted.

The term "acyl or sulfonyl substituted amino" as used herein means an amide —N($R_5$)—CO—$R_6$ and a sulfonamide —N($R_5$)—$SO_2$—$R_6$ group respectively, wherein $R_5$ is substituted or unsubstituted $C_1$-$C_6$ alkyl or substituted or unsubstituted $C_5$-$C_{12}$ aryl, preferably substituted or unsubstituted $C_1$-$C_3$ alkyl or substituted or unsubstituted $C_6$-$C_{10}$ aryl, and $R_6$ is selected from the group consisting of substituted or unsubstituted $C_1$-$C_{20}$ alkyl, substituted or unsubstituted $C_5$-$C_{20}$ aryl and camphoryl, preferably substituted or unsubstituted $C_1$-$C_{10}$ alkyl, substituted or unsubstituted $C_6$-$C_{12}$ aryl and camphoryl.

The term "alkoxy" as used herein means —O-alkyl, wherein substituted or unsubstituted alkyl is straight or branched chain and comprises 1 to 6 carbon atoms, preferably 1 to 4 carbon atoms.

The term "aryl" as used herein means substituted or unsubstituted aromatic ring systems comprising 5 to 16 carbon atoms located within the aromatic ring system. Preferably, the substituted or unsubstituted aromatic ring system comprises 1 to 3 aromatic rings, more preferably, the aromatic ring system is selected from the group consisting of phenyl, ferrocenyl, naphthyl, fluorenyl, azulenyl, indenyl, anthryl and the like, and in particular, the aromatic ring system is phenyl.

The term "substituted" as used herein means that one or more, preferably up to 5, more preferably 1-3 hydrogen atoms of a structural moiety are replaced independently from each other by the corresponding number of substituents. Typical substituents include, without being limited thereto, for example halogen, trifluoromethyl, cyano, nitro, oxo, NR', —OR', —C(O)R', —C(O)OR', —OC(O)R', —S(O)R', N(R')R", C(O)N(R')R", —$SO_2$N(R')R' and R''', wherein each of R', R" and R''' are selected from the group consisting of $C_1$-$C_6$ alkyl, $C_1$-$C_6$ alkoxy, —$(CH_2)_m$-heterocyclyl (m being 1, 2, 4 or 4) and each R' and R" may be optionally and independently further substituted with one or more of hydrogen, halogen, cyano, amino, hydroxy, $C_1$-$C_6$ alkyl and $C_1$-$C_6$ alkoxy. Specific substituents in particular include halogen such as fluoro, chloro and/or bromo, hydroxy, amino, $C_1$-$C_6$ alkyl and $C_1$-$C_6$ alkoxy, and halogenated $C_1$-$C_6$ alkyl and $C_1$-$C_6$ alkoxy such as trifluoro-methyl. It will be understood that the substituents are at positions where their introduction are is chemically possible, that is positions being known or evident to the person skilled in the art to decide (either experimentally or theoretically) without inappropriate effort whether a particular substitution is possible. For example, substituents which may be unstable or may affect reactions disclosed herein may be omitted, at least at a critical reaction step.

The term "coupling catalyst" as used herein means a compound or complex capable of catalyzing a coupling reaction.

(42) The process according to any one of items (28) to (30), wherein the compound of formula VIII

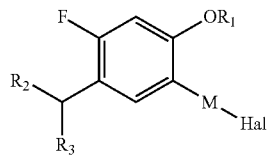

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and M is magnesium (Mg) or zinc (Zn), and Hal is selected from Cl, Br or I,
is coupled with compound of formula XI

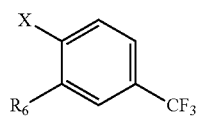

wherein $R_6$ is $CH_2Q$ or a group which can be converted to $CH_2Q$, wherein Q is selected from halogen, hydroxy, acyl or sulfonyl substituted hydroxy, amino, acyl or sulfonyl substituted amino, preferably $R_6$ is selected from the group consisting of hydroxymethyl, alkoxymethyl, halomethyl, carboxy, alkoxycarbonyl, amidocarbonyl, cyano, formyl, 2-(4,5-dihydro-1,3-oxazolyl) and X is Cl, Br, I or —OTf
to form a compound of formula XII,

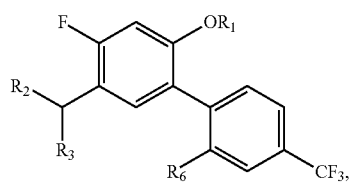

wherein $R_1$, $R_2$, $R_3$ and $R_6$ are defined as above, in the presence of a catalyst.

(43) A process for preparing a compound of formula XII,

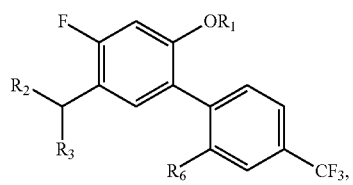

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and $R_6$ is carboxy or carboxyamide group by reacting compound of formula VI

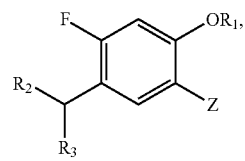

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Y or Z is Br, Cl or I
with a compound of formula XIII

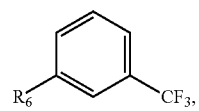

wherein $R_6$ is defined as above
in the presence of a coupling catalyst.

According to this aspect of the invention, an efficient coupling reaction is provided wherein biaryl compounds of formula XII are obtained in both high yield and purity. These biaryl compounds of formula XII represent highly valuable intermediate compounds for the preparation of pharmaceutically active agents such as anacetrapib or derivatives thereof. In said coupling reaction, readily available commercial benzoic acid derivatives such as e.g. 3-(trifluoromethyl)benzoic acid can be employed as the starting material, while conventional C—C coupling reactions of two aryl compounds require an aryl compound having a halogen or triflate substituent, wherein said halogen or triflate substituent has usually to be introduced into a commercially available aryl compound in at least one additional preparation step.

(44) The process according to item (43), wherein said coupling follows subsequent to a process as defined in any one of items (12) to (21).

(45) The process according to any one of items (41) to (44), wherein a polar aprotic solvent is present in the reaction mixture.

(46) The process according to items (45), wherein the reaction mixture is heated above 20° C.

(47) The process according to any one of items (41) to (46), wherein the coupling catalyst is selected from the group consisting of palladium-triarylphosphine, -trialkylphosphine or -aryl and alklyl substituted phosphine complexes with palladium in the zero oxidation state, salts of palladium in the presence of phosphine ligands, and metallic palladium optionally supported on a solid in a suitable solvent.

The term "alkyl" as used herein means a straight or branched chain alkyl moiety having 1 to 6 carbon atoms, preferably 1 to 4 carbon atoms.

The term "aryl" as used herein means substituted or unsubstituted aromatic ring systems comprising 5 to 16 carbon atoms located within the aromatic ring system. Preferably, the substituted or unsubstituted aromatic ring system comprises 1 to 3 aromatic rings, more preferably, the aromatic ring system is selected from the group consisting of phenyl, ferrocenyl, naphthyl, fluorenyl, azulenyl, indenyl, anthryl, and in particular, the aromatic ring system is phenyl.

(48) The process according to item (42), wherein the catalyst is a nickel (Ni) catalyst.

(49) A compound of formula VII

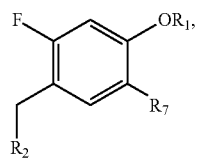

wherein $R_1$ is substituted or unsubstituted $C_1$-$C_6$ alkyl and $R_2$ is substituted or unsubstituted $C_1$-$C_6$ alkyl wherein $C_1$ has at least one hydrogen atom, and $R_7$ is selected from the group consisting of H, Cl, Br, I, —OTf, B(OH)$_2$, —MgBr and a moiety having the structural formula

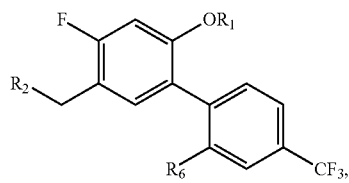

wherein $R_6$ is CH$_2$Q or a group which can be converted to CH$_2$Q group, wherein Q represents a leaving group or a group convertible to a leaving group.

(50) The compound according to item (49), wherein $R_1$ is $C_1$-$C_3$ alkyl, and $R_2$ is substituted or unsubstituted $C_1$-$C_3$ alkyl wherein $C_1$ has at least one hydrogen atom, and $R_7$ is selected from the group consisting of H, Cl, Br, I and B(OH)$_2$, preferably $R_1$ and $R_2$ are methyl (Me) and $R_7$ is selected from the group consisting of H, Br and B(OH)$_2$.

(51) A compound of formula XIV

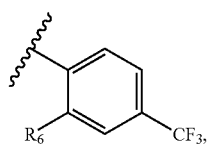

wherein $R_1$ is linear substituted or unsubstituted $C_1$-$C_6$ alkyl, preferably linear substituted or unsubstituted $C_1$-$C_3$ alkyl, more preferably $R_1$ is methyl (Me) and $R_2$ is substituted or unsubstituted $C_1$-$C_6$ alkyl wherein $C_1$ has at least one hydrogen atom, preferably $R_2$ is methyl, and $R_6$ is CH$_2$Q or a group which can be converted to CH$_2$Q group, wherein Q represents a leaving group or a group convertible to a leaving group, preferably Q is selected from the group consisting of halogen, hydroxy, acyl or sulfonyl substituted hydroxy, amino, acyl or sulfonyl substituted amino, more preferably $R_6$ is selected from the group consisting of the group consisting of hydroxymethyl, alkoxymethyl, halogenmethyl wherein halogen is Cl, Br or I, carboxy, alkoxycarbonyl, amidocarbonyl, cyano, formyl, 2-(4,5-dihydro-1,3-oxazolyl) and nitro, preferably $R_6$ is —CH$_2$Cl.

(52) A compound of formula XV

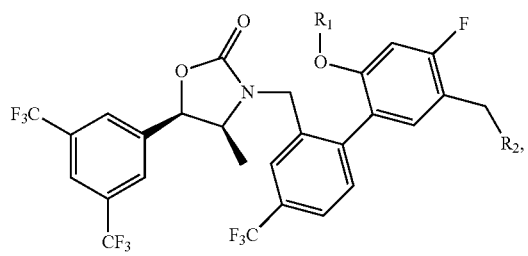

wherein $R_1$ is substituted or unsubstituted $C_1$-$C_6$ alkyl and $R_2$ is substituted or unsubstituted $C_1$-$C_6$ alkyl wherein $C_1$ has at least one hydrogen atom, preferably $R_1$ and $R_2$ is methyl.

(53) Use of a compound according to any one of items (49) to (52) as a standard for tracking desalkyl impurity/impurities through the process of preparation of pharmaceutically active agent.

The term "desalkyl impurity/impurities" as used herein means compound(s) originating from hydrogenation of unreacted starting material in form of compound of formula I in a Grignard reaction as defined in items (1) or (3) above.

The term "standard" as used herein means a compound which can be used for qualitative and/or quantitative determination of said compound e.g. as an impurity in another compound.

According to this beneficial aspect of the invention, quantitative and/or qualitative determination of compounds of formulae VII, XIV and XV in reaction products, reaction mixtures or mixtures having an unknown composition is rendered possible. For example, the aforementioned compounds can be applied in GC or HPLC analysis as standards, wherein the retention time of the standard is determined in order to identify the presence of the standard compound in a sample to be analyzed.

(54) Use of a compound of formula XVI

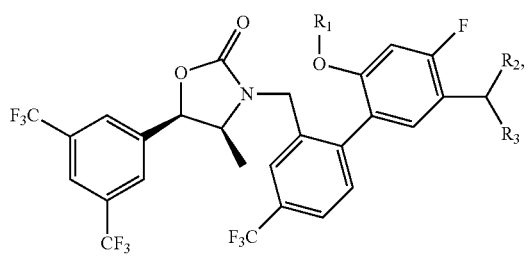

wherein $R_1$ and $R_3$ is substituted or unsubstituted $C_1$-$C_6$ alkyl and $R_2$ is substituted or unsubstituted $C_1$-$C_6$ alkyl wherein $C_1$ has at least one hydrogen atom, wherein a content of impurity in form of compound of formula XV

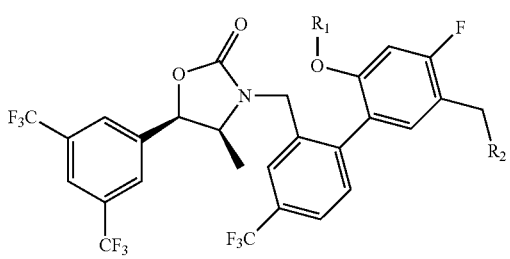

XV in compound of formula XV is less than 0.20% by weight relative to the total amount of compound of formula XVI, preferably less than 0.15%, more preferably less than 0.10%, in a process for preparing a pharmaceutical composition comprising a pharmaceutically active agent and one or more pharmaceutically acceptable excipients.

(55) Use of a compound of formula VIII' prepared according to a process as defined in any one of items (28) to (30)

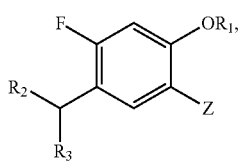

VIII' wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Z is selected from the group consisting of MgX, ZnX and X is halo, preferably Z is MgBr.

in a process for preparing a pharmaceutically active agent. The term "pharmaceutically active agent" as used herein means any active pharmaceutical ingredient intended for treatment or prophylaxis of a disease of a mammal. In general it means any active pharmaceutical ingredient that has an effect on the physiological conditions of a mammal.

(56) The use according to any one of items (53) to (55), wherein the pharmaceutically active agent is a compound of formula XVI

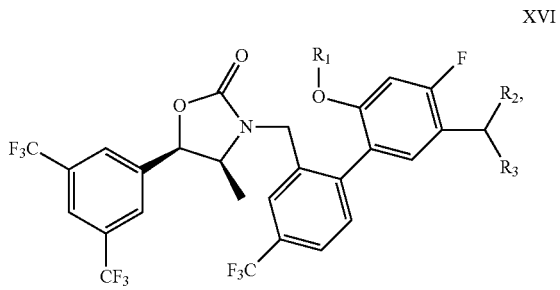

XVI wherein $R_1$ and $R_3$ is substituted or unsubstituted $C_1$-$C_6$ alkyl and $R_2$ is substituted or unsubstituted $C_1$-$C_6$ alkyl wherein $C_1$ has at least one hydrogen atom, preferably the pharmaceutically active agent is anacetrapib wherein $R_1$, $R_2$ and $R_3$ is methyl (Me).

(57) A process for producing anacetrapib, comprising the steps of:
a) providing compound of formula II

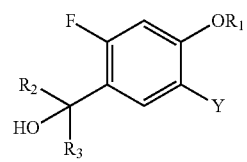

II wherein $R_1$, $R_2$ and $R_3$ are independently from each other selected from substituted or unsubstituted $C_1$-$C_6$ alkyl, and Y is Br, Cl, I or H, by a process according to any of the items (1) to (21), and
b) subjecting compound of formula II to further synthesis steps to yield anacetrapib.

(58) A pharmaceutical formulation comprising anacetrapib as a pharmaceutically active ingredient and at least one pharmaceutically acceptable excipient, wherein anacetrapib is substantially free of desmethylanacetrapib.

The term "substantially free" as used herein means that the content of desmethylanacetrapib impurity is less than 0.20% by weight relative to the total amount of anacetrapib, preferably less than 0.15% by weight, more preferably less than 0.10% by weight.

DETAILED DESCRIPTION OF THE INVENTION

In the following, the present invention will be described in more details by referring to further preferred and further advantageous embodiments and examples which are however presented for illustrative purposes only and shall not be understood as limiting the scope of the present invention.

The present invention provides an industrially applicable, economical and advantageous process for the preparation of intermediates of compound of formula II

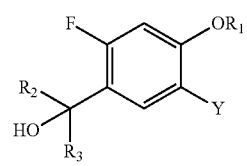

II wherein $R_1$ and $R_3$ is substituted or unsubstituted $C_1$-$C_6$ alkyl and $R_2$ is substituted or unsubstituted $C_1$-$C_6$ alkyl wherein $C_1$ has at least one hydrogen atom, and Y is Br, Cl, I or H. Compound of formula II represents a valuable intermediate for preparing pharmaceutically active agents, preferably cholesterylester transfer protein (CETP) inhibitors such as anacetrapib. The preparation process according to the invention starts from compounds of formula I

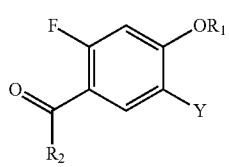

I wherein $R_1$ is substituted or unsubstituted $C_1$-$C_6$ alkyl and $R_2$ is substituted or unsubstituted $C_1$-$C_6$ alkyl wherein $C_1$ has at least one hydrogen atom, and Y is Br, Cl, I or H, such as e.g. 1-(2-fluoro-4-methoxyphenyl)ethanone (FMAP), which represent readily available economical commercial starting materials used in the prior art. However, it has been found and shown that following the prior art process for the synthesis of anacetrapib starting from FMAP lead to a formation of a desalkyl impurity such as e.g. desmethyl impurity (DMAP). Because the desalkyl impurities have only small variation in the structure, they have often very similar physical properties and practically identical chemical properties compared to intermediates for preparation of anacetrapib and are thus hard to remove from the final product.

It was surprisingly found by the present invention that the presence of a suitable second solvent, especially the presence of a second solvent being selected from the group consisting of dichloromethane (DCM), toluene or 1,2-dimethoxyethane (DME), in a reaction medium comprising a first solvent, starting material FMAP and Grignard reagent, provides for a significantly improved chemoselectivity of Grignard reagent for the addition to FMAP while the enolization of FMAP is suppressed, and therefore, the obtained product is essentially free of starting material FMAP and thus has an exceptional purity compared to FMOL prepared by conventional Grignard reaction. Therefore, the present process provides for preparation of intermediates for pharmaceutically active agent such as anacetrapib in a industry friendly manner and provides excellent options to use economical and commercially available starting material for the preparation of valuable intermediate compounds having a high degree of purity in view of desmethyl impurities.

In an alternative process for preparing compound of formula II, the formation of byproducts in form of formula $III_1$

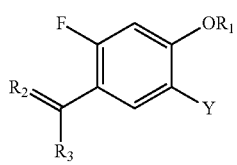

$III_1$ and/or compound of formula $III_2$

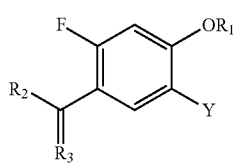

$III_2$ wherein $R_1$ is substituted or unsubstituted $C_1$-$C_6$ alkyl, $R_2$ and $R_3$ are independently from each other selected from substituted or unsubstituted $C_1$-$C_6$ alkyl and alkylidene and Y is Br, Cl, I or H, is efficiently suppressed by quenching a Grignard reaction mixture with an organic solvent selected from the group consisting of chloroform and $C_1$-$C_6$ alcohols, preferably methanol.

On the other hand, the dehydration of compound II can be a favorable process, because compounds of formula $III_1$ and/or $III_2$ are hydrogenated to IV

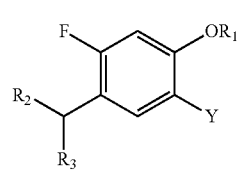

IV wherein $R_1$ and $R_3$ is substituted or unsubstituted $C_1$-$C_6$ alkyl and $R_2$ is substituted or unsubstituted $C_1$-$C_6$ alkyl wherein $C_1$ has at least one hydrogen atom, and Y is Br, Cl, I or H, by hydrogenation, at faster reaction rates and/or requires lower loading of catalysts. Therefore, there is no need for eliminating dehydration and isolation of this intermediate, the result of the reaction is simply telescoped into the next step with partial or essential removing of solvents and diluting the residue with the solvent for catalytic hydrogenation.

Furthermore, according to another preferred aspect of the invention, desalkyl compounds such as compound of formula VII'

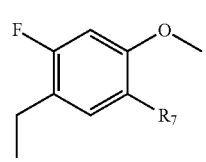

VII' wherein $R_7$ is selected from the group consisting of H, Cl, Br, I, and $B(OH)_2$, and compound of formula XIV'

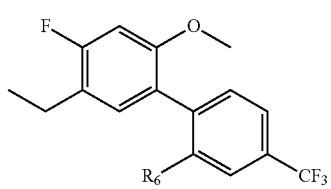

XIV' wherein $R_6$ is $CH_2Q$ or a group which can be converted to $CH_2Q$ group, wherein Q represents a leaving group or a group convertible to a leaving group, preferably Q is selected from the group consisting of halogen, hydroxy, acyl or sulfonyl substituted hydroxy, amino, acyl or sulfonyl substituted amino, and compound of formula XV'

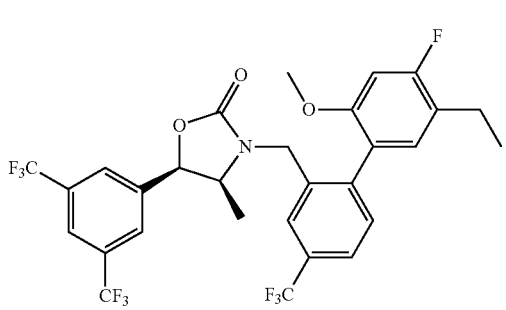

in particular XV' (DMAP), have been specifically prepared, since these compounds represent valuable standard compounds for quantitative and/or qualitative tracking of desmethyl impurities in a process for preparing a pharmaceutically active agent.

Scheme 8 illustrates a preferred embodiment of the process according to the present invention wherein compounds of formula IV in which $R_1$, $R_2$ and $R_3$ is methyl (Me) and Y is H (MIP) is prepared, among others via compound of formula II in which $R_1$, $R_2$ and $R_3$ is methyl (Me) and Y is H (FMOL) and/or compound of formula III in which $R_1$ and $R_3$ is methyl (Me), $R_2$ is methylene and Y is H (MIPEN). However, it is understood that this process is also applicable to compounds of formulae I to IV having other substituents $R_1$, $R_2$ and Y than shown in Scheme 8.

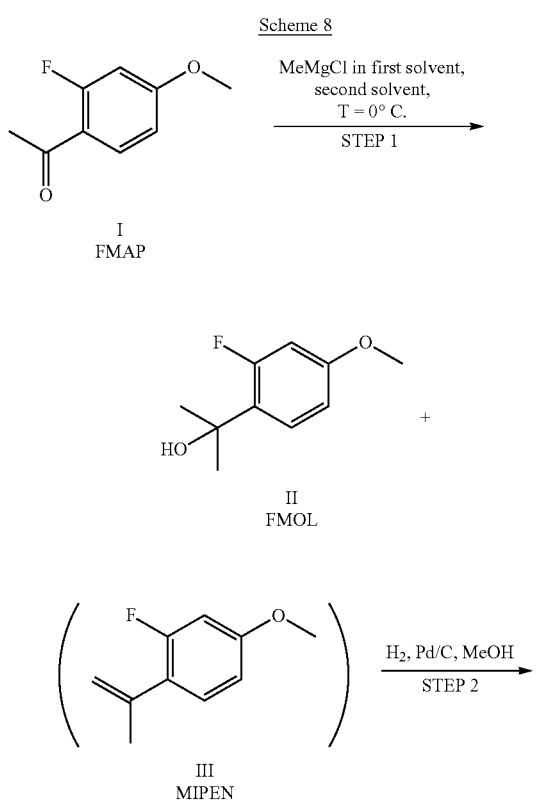

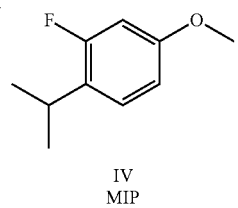

In the first step of this embodiment, compound II in which $R_1$, $R_2$ and $R_3$ is methyl (Me) and Y is H (FMOL) is synthesized from I wherein $R_1$ and $R_2$ is methyl and Y is H (FMAP) using a second solvent such as e.g. dichloromethane (DCM), toluene or 1,2-dimethoxyethane (DME) for Grignard reaction. It was surprisingly found that the presence of such a second solvent significantly increased the chemoselectivity (addition versus enolization) of the reaction compared to conventional Grignard reactions wherein only one solvent (the first solvent) is used. Typically, Grignard reaction is carried out in an ether as the solvent, such as e.g. tetrahydrofuran, methyl tert-butyl ether, diethyl ether or 1,4-dioxane. Thus, when applying a second solvent in the Grignard reaction, the obtained product FMOL was substantially free of starting material FMAP, an impurity which is converted to desmethyl impurities in subsequent steps, wherein said desmethyl impurities are difficult to remove from the reaction products.

In general Grignard reaction is carried out under an inert atmosphere, preferably under an argon or nitrogen atmosphere. According to a beneficial aspect of the invention, a second mixture of acetophenone FMAP admixed in a second solvent is contacted with a first mixture of Grignard reagent MeMgCl admixed in a first solvent such as e.g. tetrahydrofuran, preferably contacting is carried out by dropwise addition. The second solvent is selected from the group consisting of dichloromethane (DCM), toluene and 1,2 dimethoxyethane (DME). It was surprisingly found by the invention that the presence of a second solvent significantly increases the chemoselectivity of Grignard reaction, which in turn provides for a product in form of FMOL being essentially free of starting material FMAP.

Since reaction of FMAP with a Grignard reagent is exothermic, wherein elevated temperatures have a negative effect on Grignard reaction, contacting of first and second solution is carried out such that the temperature of the reaction mixture is preferably kept below 20° C., preferably below 5° C. Furthermore, preferably 1.0 to 2.0 equivalents of Grignard reagent are used, more preferably 1.2 to 1.6.

According to an alternative aspect of the invention, Grignard reaction is quenched with an organic solvent in order to selectively obtain FMOL without dehydrated byproduct MIPEN, wherein the organic solvent for quenching is selected from the group consisting of chloroform or $C_1$-$C_6$ alcohols, preferably methanol.

Preferably, the concept of applying a second solvent in Grignard reaction is combined with the concept of controlling formation of dehydrated byproduct III in which $R_1$ and $R_3$ is methyl (Me), $R_2$ is methylene and Y is H (MIPEN) by choosing an suitable quenching solvent in order to obtain compound FMOL essentially free of both starting material FMAP and dehydrated byproduct MIPEN.

The alkylated product in form of FMOL may be partially dehydrated to a compound of formula MIPEN during the isolation process. It was surprisingly found by the invention that dehydration of FMOL to MIPEN can be controlled by selecting appropriate quenching solvent, temperature and rate of quenching solvent addition. Chloroform and methanol turned out to be particularly advantageous solvents for quenching Grignard reaction in order to effectively prevent formation of dehydrated byproduct MIPEN, and thus, FMOL being substantially free of MIPEN is obtained.

On the other hand, the formation of dehydrated byproduct MIPEN may be advantageous, since MIPEN compared to FMOL is hydrogenated to MIP at faster reaction rates and/or requires lower loading of catalysts. Therefore, in case hydrogenation of intermediate compound FMOL is intended in a subsequent step, there is no need for preventing formation of dehydrated byproduct MIPEN, rather formation of MIPEN is advantageous. The amount of dehydrated byproduct MIPEN is significantly increased when applying conventional quenching conditions, that is no aforementioned organic solvent for quenching is used, but merely aqueous inorganic acids such as 2 M hydrochloric acid, while no attention is paid to keep the reaction mixture within a certain, low temperature range.

According to a preferred embodiment, the crude product in form of a mixture of FMOL and MIPEN is simply telescoped into the next step, wherein a laborious purification step is saved. MIPEN or mixtures of MIPEN and FMOL are then reduced to MIP using hydrogen and catalyst derived from palladium, platinum or nickel in methanol, ethanol, acetic acid or the like. Preferred conditions for this reduction are from 1 to 10 bar hydrogen, 5% palladium on charcoal in ethanol or methanol, optionally in the presence of concentrated hydrochloric acid at 40° C.

The compound of formula MIP formed in the second step of this embodiment according to this procedure is substantially free of desmethyl impurities, preferably it is substantially free of desmethyl impurity 3-fluoro-4-ethylanisole (MET).

A further preferred embodiment of the process according to the present invention is illustrated in Scheme 9 wherein compounds of formulae VI in which $R_1$, $R_2$ and $R_3$ is methyl and Y is Br (BrMIP) are prepared, wherein preparation starts with compound of formula I wherein $R_1$ and $R_2$ is methyl and Y is H (FMAP). However, it is understood that this process is also applicable to compounds of formulae I to VI having other substituents $R_1$, $R_2$ and $R_3$ and Y than shown in Scheme 9.

Scheme 9

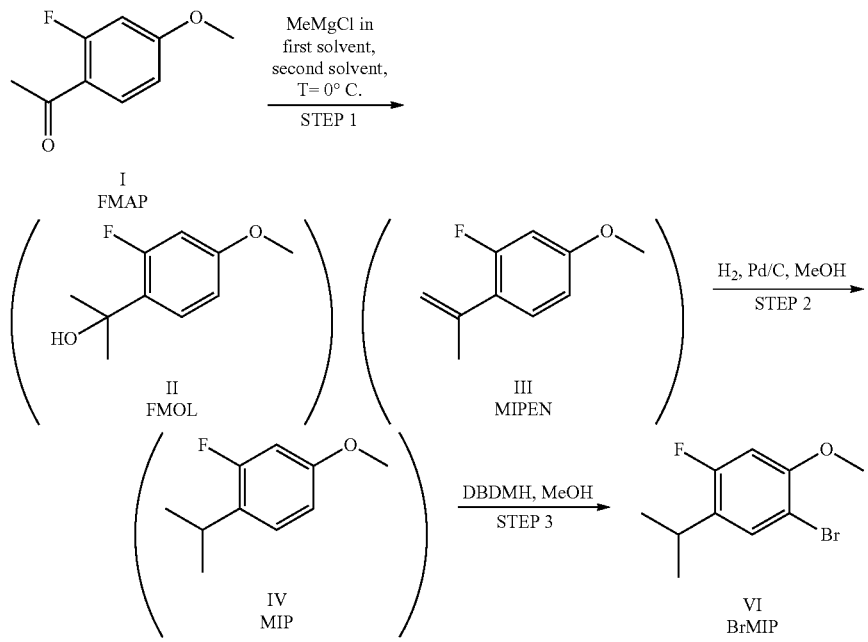

Steps 1 and 2 of this embodiment are in accordance with steps 1 and 2 of the embodiment as elucidated for Scheme 8. Catalytic hydrogenation in step 2 is preferably carried out at 1 to 10 bar hydrogen, preferably 3 bar, wherein the hydrogenation catalyst is preferably palladium on charcoal used in an amount of preferably 0.10 to 0.30 mol % relative to FMAP or the total amount of FMOL and MIPEN.

The reactions of the second and the third step of this embodiment can be advantageously carried out as a one pot reaction, wherein the crude product of FMOL/MIPEN resulting from step 1 can be directly used as the starting material for the second step and third step. In a one pot step the crude FMOL/MIPEN is converted to BrMIP without isolation and/or purification of and MIP. Hence, according to this beneficial embodiment, bromination is advantageously carried out in the same solvent used in the second reaction step, wherein no laborious and energy consuming removal of solvent(s) is necessary. In this approach, there is no need of isolation of MIP the second step of this embodiment can be advantageously finished by merely removing hydrogenation catalyst from the reaction mixture, preferably by means of filtration. After removal of the hydrogenation catalyst, MIP dissolved in the solvent already applied in step 2 is directly transferred to bromination, that is step 3. For a one-pot reaction, the aforementioned solvent for step 2 is selected with the proviso that it is also suitable in the halogenation reaction of step 3, preferably the solvent is selected from the group consisting of $C_1$-$C_6$ alcohols or $C_1$-$C_6$ alkyl esters of $C_1$-$C_6$ carboxylic acids as the solvent, preferably $C_1$-$C_3$ alcohols or $C_1$-$C_3$ alkyl esters of $C_1$-$C_3$ carboxylic acids, more preferably the solvent is selected from the group consisting of methanol, ethanol, isopropyl alcohol, ethyl acetate, isopropyl acetate and acetic acid, even more preferably the solvent is methanol. Halogenation reaction of step 3 is preferably carried out by using 1,3-dibromo-5,5-dimethylhydantoin (DBDMH) as the halogenating agent.

Owing to the advantageous one-pot reaction strategy, the total yield of this 3-step process is significantly increased, since isolation and purification steps for FMOL and MIP can be advantageously omitted, wherein yield is at least 20% higher compared to analogous, conventional prior art processes comprising one or more isolation and/or purification steps.

Unexpectedly, the compound of formula BrMIP prepared according to this procedure is substantially free of desmethyl impurities, preferably it is substantially free of desmethyl impurity 2-bromo-5-fluoro-4-ethylanisole (BrMET).

Still another preferred embodiment is illustrated in Scheme 10 wherein biaryl compounds of formulae XII' and XII" in which $R_1$, $R_2$ and $R_3$ is methyl (Me) are prepared, wherein preparation starts with compound of formula VI in which $R_1$, $R_2$ and $R_3$ is methyl (Me) and Y is Br (BrMIP). However, it is understood that this process is also applicable to compounds of formulae VI, VIII, IX and XII having other substituents $R_1$, $R_2$, $R_3$ and Y than shown in Scheme 10.

obtain compound of formula XII' under Suzuki coupling conditions. The particularly preferred catalyst-ligand systems for the Suzuki couplings are $Pd(OAc)_2/PPh_3$ or 1,1-bis(di-tertbutylphosphino)ferrocene palladium dichloride. Biaryl compound XII' may be converted to compound XII" wherein $R_6$ is converted to $R_6'$ comprising a leaving group Q which provides for building to heterocycle of formula XVII

XVII

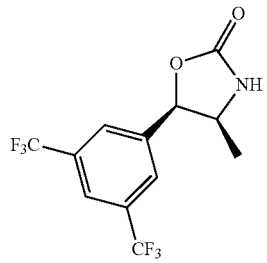

to form anacetrabip (ACP) of formula XVI wherein $R_1$, $R_2$ and $R_3$ are methyl groups.

Alternatively, MIPB may be advantageously prepared in a one pot process by using intermediate MgBrMIP which is Scheme 10

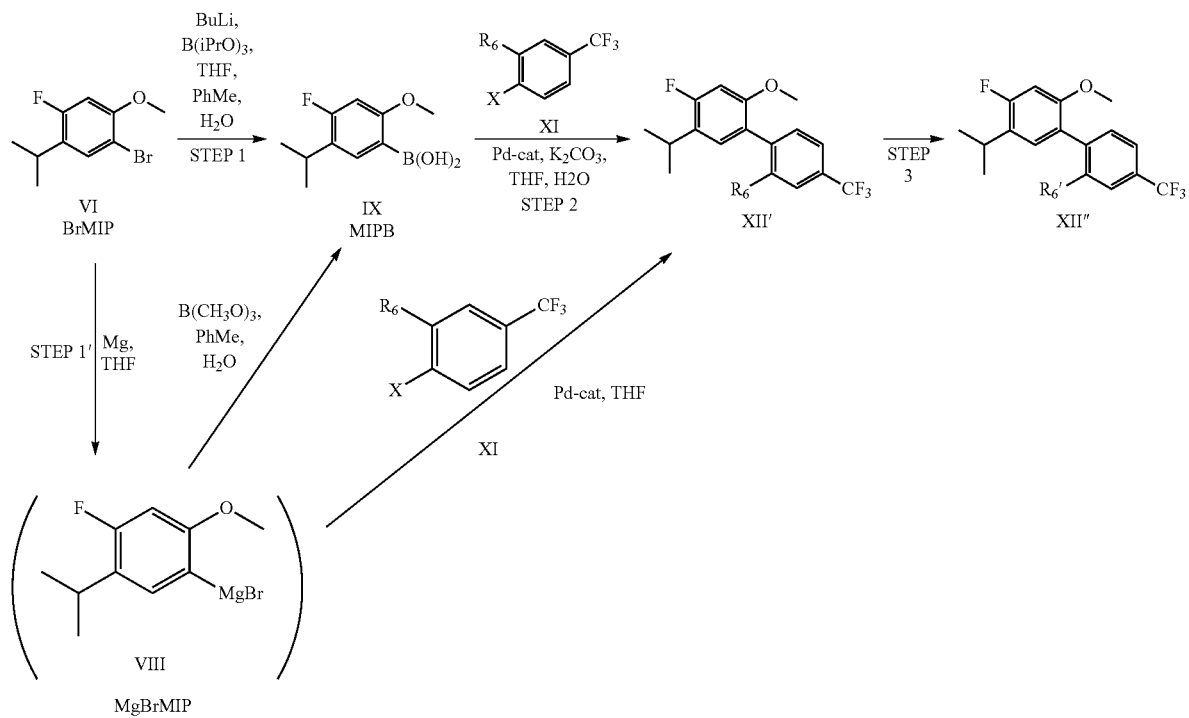

Compounds of formula XII'/XII", wherein $R_1$, $R_2$ and $R_3$ are as defined above can be prepared according to the versatile synthetic route depicted in Scheme 10. In the first step of this advantageous embodiment, BrMIP is treated with a trialkyl borate, preferably triisopropyl borate, in the presence of a strong base in an inert aprotic solvent or mixture of solvents in order to obtain an boric ester which is hydrolized with diluted aqueous inorganic acid to yield a compound of formula MIPB. This compound can be coupled with a compound XI wherein $R_6$ and X are defined as in the above items to preferably prepared by treating BrMIP with activated magnesium in THF in order to obtain a solution of arylmagnesium bromide MgBrMIP. MgBrMIP is then added to a solution of trialkyl borate, preferably trimethyl borate in an inert aprotic solvent or mixture of solvents, preferably toluene. Preferably, reaction temperature is above −10° C., more preferably above 0° C. Surprisingly, the present approach of MIPB is accomplished at elevated temperatures of above 0° C. In contrast to that, the prior art approach using buthyl lithium (BuLi) and isopropyl borate as described in patent application WO 2007/

005572 requires temperatures below −50° C. in order to ensure an undisturbed conversion to MIPB.

Arylmagnesium compound MgBrMIP is a versatile intermediate compound, since it can e.g. be also coupled with compound of formula XI without converting to boronic compounds such as MIPB, provided that substituent $R_6$ is suitably selected from groups being inert in Grignard reaction conditions.

In order to provide intermediates particularly suitable for preparing inhibitors of cholesteryl ester transfer protein (CETP), preferably anacetrapib, a moiety comprised in $R_6$ of compound of formula XII' is preferably converted to a group $CH_2Q$ which is capable of being reacted with another compound, preferably $CH_2Q$ is a group enabling coupling to compound of formula XVII as depicted above. That is, biaryl compound XII' wherein $R_6$ is a group comprising at least one group which is convertible into a leaving group is converted to compound XII" wherein $R_6$' comprising a leaving group Q originates from $R_6$. For example, a hydroxymethyl group can be converted to chloromethyl or bromomethyl by treating with corresponding sulphur, phosphorus, oxalyl halide, phosgene derivative or hydrohalic acid, or it is sulfonated to give a leaving sulfonyloxy group. Furthermore, a cyano group can be converted to aminomethyl group by reduction, preferably by hydrogenation on Raney Ni and further to the sulfonimide leaving group. An alkoxymethyl such as methoxymethyl group can be demethylated and debenzylated with boron bromides, aluminium bromides or hydrobromic acid to give bromomethyl substituted compounds, and an alkoxycarbonyl or formyl group can be reduced to the hydroxymethyl group, which is further transformed as said above.

In a still further preferred embodiment, a commercially available substituted benzoic acid compound such as compound XIII' wherein $R_6$ is COOH (FBA) is directly coupled with compound of formula VI in which $R_1$, $R_2$ and $R_3$ is methyl (Me) and Y is Br (BrMIP) by the method of direct ortho-arylation of a benzoic acid as described in J. Am. Chem. Soc. 2007, 129, 9879-9884.

This embodiment is illustrated in Scheme 11, wherein biaryl compound of formula XII wherein $R_1$, $R_2$ and $R_3$ is methyl (Me) and $R_6$ is —COOH (BFK) is prepared starting from compound BrMIP. However, it is understood that this process is also applicable to compounds of formulae VI, XIII and XII having other substituents $R_1$, $R_2$, $R_3$, $R_6$ and Y than shown in Scheme 11.

Scheme 11

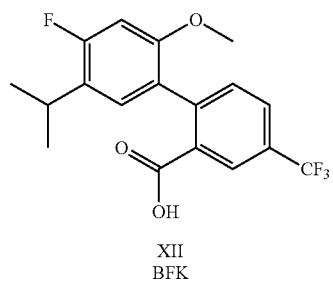

XII
BFK

In prior art examples, an excess of aryl halide (usually 3 equivalents) was required due to hydrodehalogenation of aryl halide starting material. To our knowledge, there is no disclosure reporting about successful cross coupling of anisole substrates with benzoic acids. Rather, it was reported in J. Am. Chem. Soc. 2007, 129, 9879-9884 that a coupling of a structurally simple 4-chloroanisole suffered substantial hydrodehalogenation with all benzoic acids tested. Contrary to the aforementioned prior art teaching, it was surprisingly found by the present invention that preparation of compound of formula BFK by coupling of anisole derivative BrMIP and benzoic acid derivative BFA works smoothly when applying the special conditions according to the present invention, wherein compound of formula XII is obtained in considerable high yields of up to 60%. The reaction is preferably carried out with an excess of benzoic acid FBA, most preferably an excess of about 10 mol % relative to compound of formula BrMIP. Preferably, a coupling catalyst selected from the group of Pd-catalysts such as $Pd(OAc)_2$, $PdCl_2$ or the like is applied, wherein said catalyst preferably has bulky phosphine ligands such as $tBu_3P$, $nBuAd_2P$, $cHex_3P$ or the like. Furthermore, coupling is preferably carried out in an aprotic solvent selected from the group consisting of dimethylformamide (DMF), N-methylpyrrolidone (NMP), acetonitrile and toluene, wherein reaction is carried out at temperatures higher then 50° C., preferably higher then 100° C.

According to a preferred embodiment, XII wherein $R_1$, $R_2$ and $R_3$ is methyl (Me) and $R_6$ is —COOH is converted to a group $R_6$' capable of being reacted with another compound, preferably $R_6$' is a group enabling coupling to a heterocycle of compound of formula XVII. For example, biaryl compound BFK may be first converted to an alkyl or aryl ester and then reduced to a corresponding alcohol. Said alcohol can be further converted to a leaving group such as Cl, Br, I or sulfonate esters by methods known in the art.

In the preferred embodiment illustrated in Scheme 12, biaryl compound of formula XII wherein $R_1$, $R_2$ and $R_3$ is methyl (Me) and $R_6$ is —$CH_2$—$OCH_3$ is prepared starting from compound of formula VIII wherein $R_1$, $R_2$ and $R_3$ is methyl (Me), M is Mg and Y is Br (MgBrMIP). However, it is understood that this process is also applicable to compounds of formulae XI, VIII, XII' and XII" having other substituents $R_1$, $R_2$, $R_3$, $R_6$ and Y than shown in Scheme 12.

Scheme 12

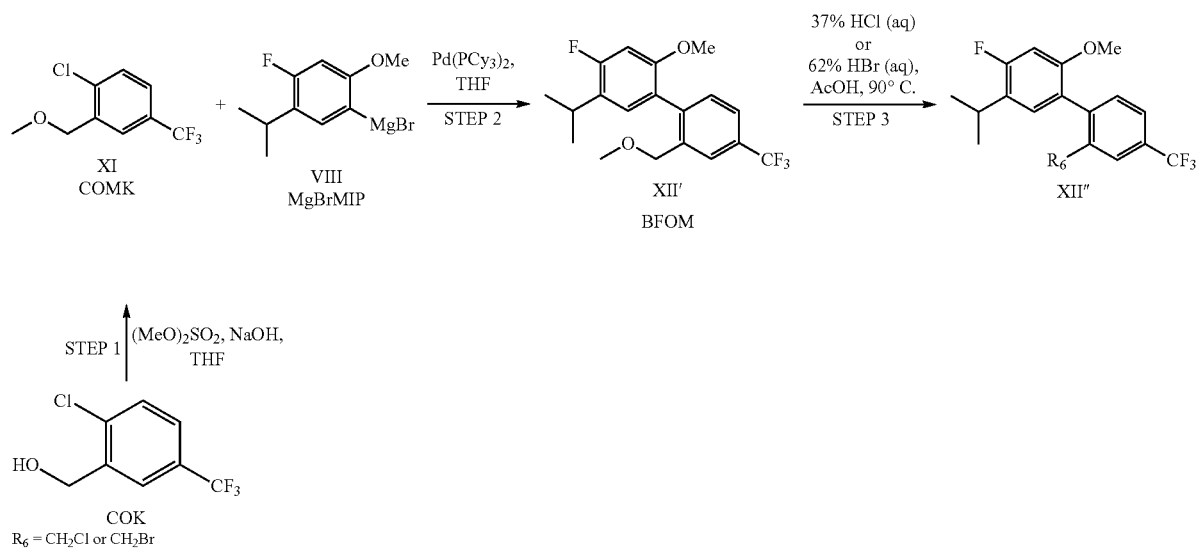

According to this embodiment, in a first step, 1-chloro-2-(methoxymethyl)-4-(trifluoromethyl)benzene (COMK) is readily synthesized from commercially available (2-chloro-5-(trifluoromethyl)phenyl)methanol (COK) etherified, e.g by using dimethyl sulfate and NaOH in THF. In a second step, Grignard compound of formula MgBrMIP is coupled to COMK by Kumada coupling, wherein coupling is preferably carried out by heating the reaction mixture to up to 80° C., preferably heating is provided by microwaves. The coupling catalyst applied is preferably Pd(PCy$_3$)$_2$, and particularly, THF is used as the solvent. Preferably, biaryl of formula XII' wherein R$_6$ is —CH$_2$—OCH$_3$ and R$_2$ and R$_3$ is Me (BFOM) is prepared. In a third step, BFOM can be smoothly converted to a compound of formula XII" wherein R$_6$' is —CH$_2$Q' in which Q is Cl or Br, by e.g. using HCl or HBr in acetic acid, respectively.

In a yet still further preferred embodiment as illustrated in Scheme 13 below, compound of formula XV wherein R$_1$ and R$_2$ is methyl (Me) and R$_3$ is H (desmethyl anacetrapib (DMAP)) is prepared starting from compound of formula I in which R$_1$ and R$_2$ is methyl (FMAP). However, it is understood that this process is also applicable to compounds of formulae I, VII, XIV and XV having other substituents R$_1$, R$_2$, R$_3$, R$_6$ and Y than shown in Scheme 13.

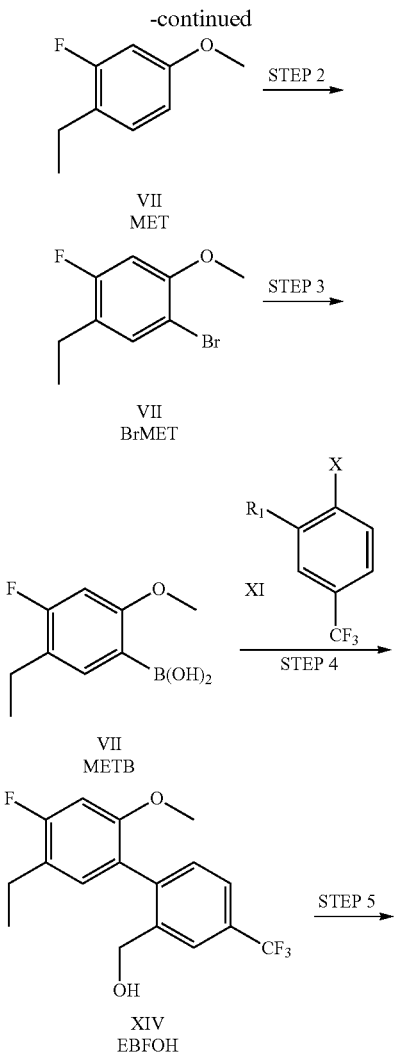

Scheme 13

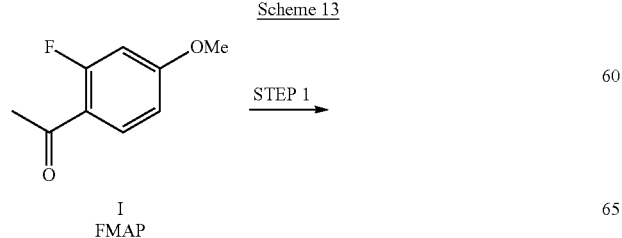

-continued

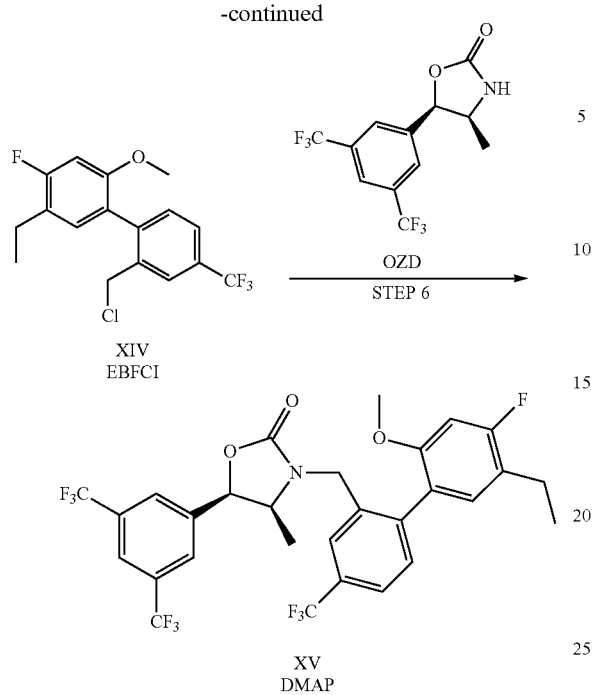

XIV
EBFCI

XV
DMAP

In a first step of this embodiment, commercially available acetophenone FMAP is reduced to MET, preferably by catalytic hydrogenation. This intermediate is brominated in the next step in order to obtain compound BrMET, which then converted to boronic acid METB. Boronic acid METB is then coupled with the commercially available benzyl alcohol XI wherein $R_6$ is $CH_2OH$ and X is Cl, preferably by means of Suzuki coupling, to yield the desired biphenyl EBFOH. Biphenyl alcohol EBFOH is converted to EBFCI and then reacted with heterocycle OZD in the presence of base to finally obtain compound of formula XV' (desmethyl anacetrapib DMAP). All aforementioned compounds of formula MET, BrMET, METB, BFOH, EBFCI, DMAP represent highly valuable materials e.g. for tracking desmethyl impurities e.g. in a synthetic route for preparing a pharmaceutically active agent such as anacetrapib.

In the following, embodiments (A) to (F) are elucidated in order to exemplify particularly preferred routes for preparing anacetrapib or intermediate compounds for the synthesis of anacetrapib and corresponding desmethyl impurities.

According to a preferred embodiment (A) of the present invention, a process for preparing a compound of formula ACP,

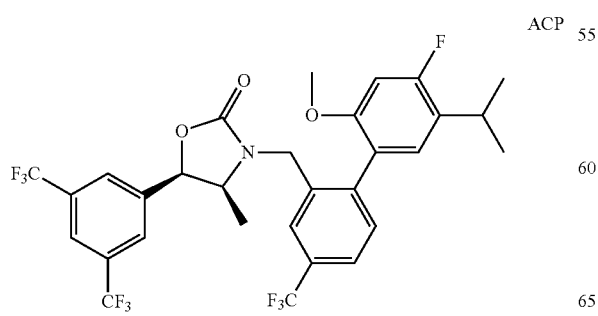

ACP substantially free of a desmethyl impurity of formula DMAP

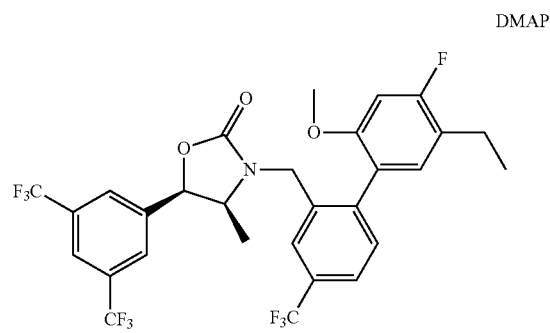 [SMILES: CCc1cc(-c2ccc(C(F)(F)F)cc2CN2C(=O)O[C@H](c3cc(C(F)(F)F)cc(C(F)(F)F)c3)[C@@H]2C)c(OC)cc1F]

DMAP is provided comprising the steps of:
a) treating 1-(2-fluoro-4-methoxyphenyl)ethanone (FMAP),

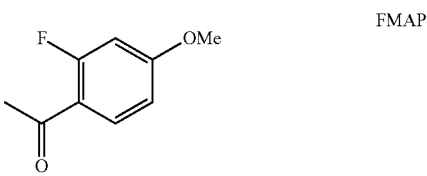

FMAP with a methylmagnesium halide in the presence of dichloromethane, toluene or 1,2-dimethoxyethane followed by quenching and evaporation of volatile material to obtain a highly concentrated solution of 2-(2-fluoro-4-methoxyphenyl)propan-2-ol (FMOL)

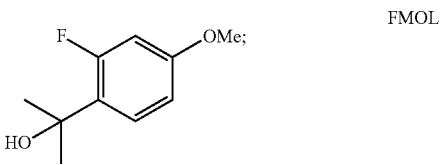

FMOL b) further hydrogenating the product of step a) in the presence of a hydrogenation catalyst, preferably a hydrogenation catalyst supported on a solid, forming order to obtain 2-fluoro-1-isopropyl-4-methoxybenzene (MIP)

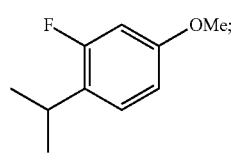

MIP c) converting MIP to 1-bromo-4-fluoro-5-isopropyl-2-methoxybenzene (BrMIP),

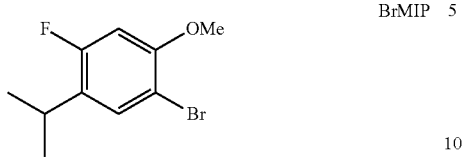

BrMIP by contacting with a bromination agent, preferably the bromination agent is a N-bromo substituted reagent, more preferably 1,3-dibromo-5,5-dimethylhydantoin (DBDMH);

d) treating BrMIP
(i) with reactive metal species to obtain intermediate organometallic intermediate of compound of formula VIII',

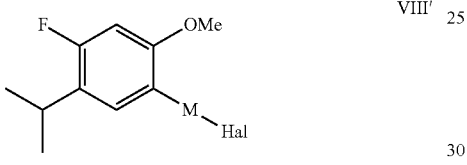

VIII' wherein M is a metal substituent, preferably selected from Li, Zn or Mg, and Hal is Cl, Br or I, and (ii) converting the compound of formula VIII' to a compound of formula IX',

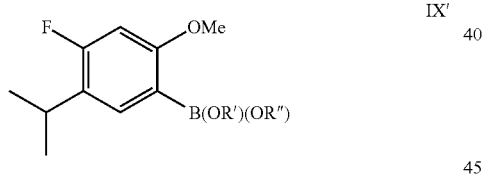

IX' wherein R' and R" are selected from alkyl or represent alkylene e) coupling of the compound formula IX' with a compound of formula XI,

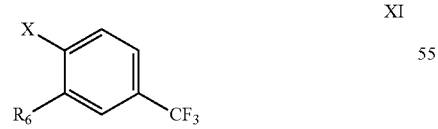

XI $R_6$ is $CH_2Q$ or a group which can be converted to $CH_2Q$ group, wherein Q represents a leaving group or a group convertible to a leaving group, preferably Q is selected from the group consisting of halogen, hydroxy, acyl or sulfonyl substituted hydroxy, amino, acyl or sulfonyl substituted amino, more preferably $R_2$ is selected from the group consisting of hydroxymethyl, alkoxymethyl, halogenmethyl wherein halogen is Cl, Br or I, carboxy, alkoxycarbonyl, amidocarbonyl, cyano, formyl, 2-(4,5-dihydro-1,3-oxazolyl) and nitro, in the presence of a transition metal catalyst preferably selected from the group consisting of palladium-triarylphosphine, -trialkylphosphine or -aryl and alkyl substituted phosphine complexes with palladium in the zero oxidation state, salts of palladium in the presence of phosphine ligands, and metallic palladium optionally supported on a solid in a suitable solvent, preferably applying heating, more preferably heating by microwaves to form a compound of formula XII',

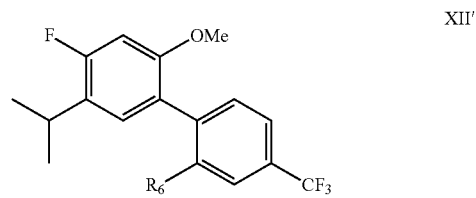

XII' wherein $R_6$ is defined as above;

f) converting the compound of formula XII' to a compound of formula XII",

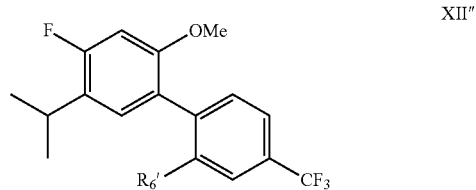

XII"

wherein $R_6$ comprises a $CH_2Q$ group wherein a leaving group Q is preferably selected from the group consisting of halo, sulfonyl or acyl substituted hydroxyl or amino;

g) coupling compound of formula XII" with a compound of formula XVII,

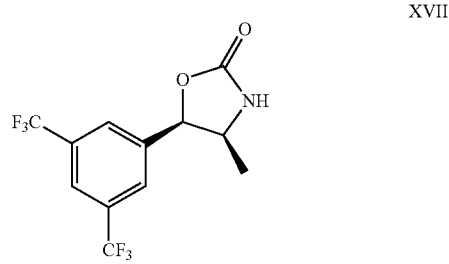 [SMILES: C[C@@H]1NC(=O)O[C@@H]1c1cc(C(F)(F)F)cc(C(F)(F)F)c1]

XVII in the presence of a base
to yield a compound of formula ACP,

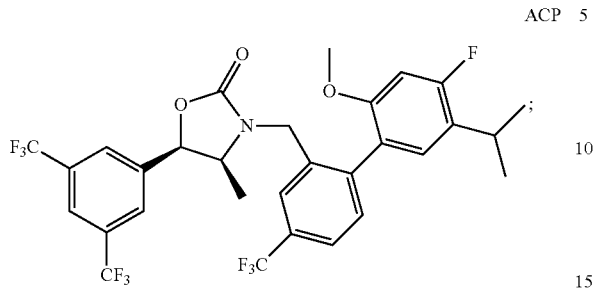
ACP h) optionally purifying the compound of formula ACP by re-precipitation methods in order to reduce level of other impurities.

According to a further embodiment (B), intermediate product FMOL is not isolated, but it is transferred into the next step in form of a evaporation residue or a concentrated solution, wherein said residue or solution is diluted with a solvent suitable for the following hydrogenation reaction.

According to embodiment (C), a process for preparing a compound of formula ACP is provided, wherein the steps b) and c) of embodiment (A) are replaced by:
i) a one pot conversion of FMOL

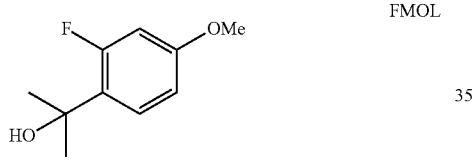
FMOL to BrMIP

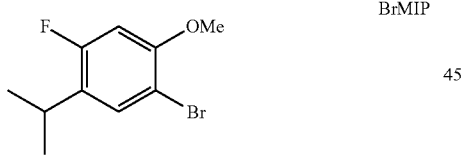
BrMIP by catalytic hydrogenation, wherein the hydrogenation catalyst is removed from the resulting reaction mixture before bromination is carried out.

According to beneficial embodiment (D), a process for preparing compound of formula ACP is provided, wherein the steps b) and c) of embodiment (A) are replaced by:
j) a one pot conversion of a mixture of FMOL

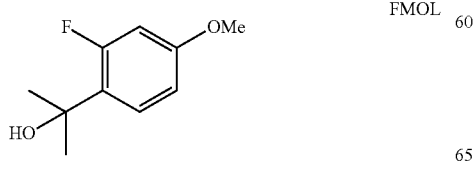
FMOL and 2-fluoro-4-methoxy-1-(prop-1-en-2-yl)benzene (MIPEN)

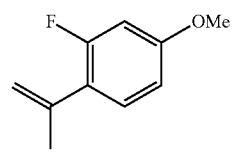
MIPEN to BrMIP

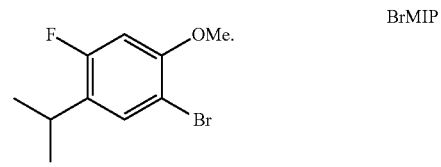
BrMIP

According to a further preferred embodiment (E), a process for preparing a compound of formula ACP is provided wherein step d) of embodiment (A) is replaced by:
k) treating the compound formula of BrMIP with a suitable elemental metal or metal salt selected from the group consisting of magnesium or zinc, or first with butyllithium, Grignard reagent, magnesium or lithium and then followed by $ZnX_2$ to form a compound of formula VIII'.

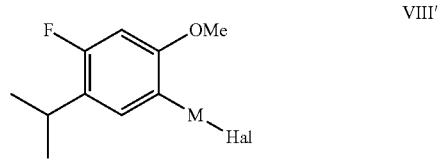
VIII' wherein M is Mg or Zn and Hal is Cl, Br or I;
and coupling of compound formula VIII' with a compound of formula XI,

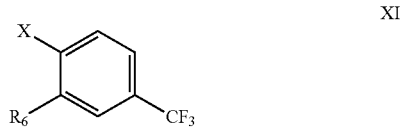
XI $R_6$ is $CH_2Q$ or a group which can be converted to $CH_2Q$ group, wherein Q represents a leaving group or a group convertible to a leaving group, preferably Q is selected from the group consisting of halogen, hydroxy, acyl or sulfonyl substituted hydroxy, amino, acyl or sulfonyl substituted amino, more preferably $R_6$ is selected from the group consisting from group consisting of hydroxymethyl, alkoxymethyl, halogenmethyl wherein halogen is Cl, Br or I, carboxy, alkoxycarbonyl, amidocarbonyl, cyano, formyl, 2-(4, 5-dihydro-1,3-oxazolyl) and nitro, to yield a compound of formula XII',

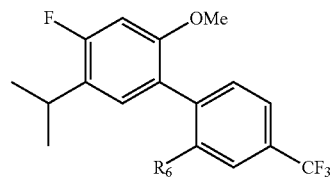

XII' wherein $R_6$ is defined as above.

According to a still further preferred embodiment (F), a process for preparing a compound of formula DMAP,

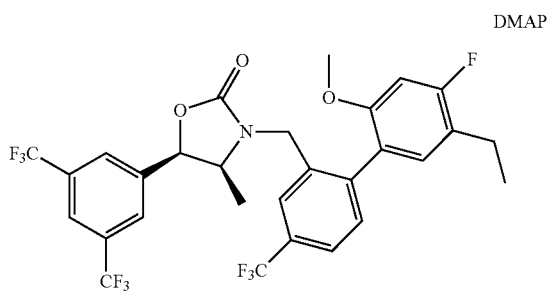 [SMILES: CCc1cc(-c2ccc(C(F)(F)F)cc2CN2C(=O)O[C@H](c3cc(C(F)(F)F)cc(C(F)(F)F)c3)[C@@H]2C)c(OC)cc1F]

DMAP is provided, wherein said process comprises the steps of:
(i) converting FMAP

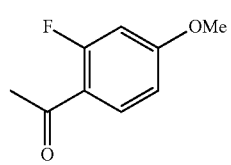

FMAP to 1-ethyl-2-fluoro-4-methoxybenzene (MET)

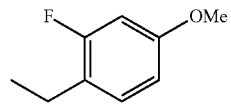

MET by hydrogenation in the presence of a hydrogenation catalyst, preferably hydrogenation catalyst is palladium supported on a solid, more preferably palladium on charcoal;
(ii) converting MET to 2-bromo-5-fluoro-4-ethylanisole (BrMET)

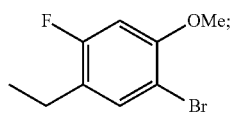

BrMET (iii) converting BrMET to a compound 5-ethyl-4-fluoro-2-methoxybenzenboronic acid (METB)

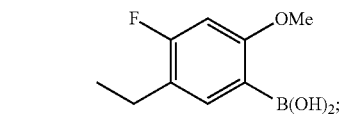

METB (iv) coupling METB with a compound of formula XI,

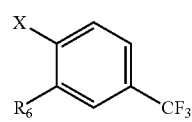

XI $R_6$ is $CH_2Q$ or a group which can be converted to $CH_2Q$ group, wherein Q represents a leaving group or a group convertible to a leaving group, preferably Q is selected from the group consisting of halogen, hydroxy, acyl or sulfonyl substituted hydroxy, amino, acyl or sulfonyl substituted amino, more preferably $R_2$ is selected from the group consisting of hydroxymethyl, alkoxymethyl, halogenmethyl wherein halogen is Cl, Br or I, carboxy, alkoxycarbonyl, amidocarbonyl, cyano, formyl, 2-(4,5-dihydro-1,3-oxazolyl) and nitro, and X is Cl, Br or I, to obtain a compound of formula XIV',

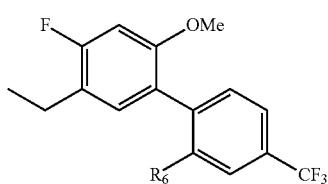

XIV' wherein $R_6$ is defined as above;
(v) converting the compound of formula XIV' to a compound of formula XIV'',

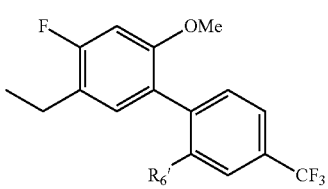

XIV'' wherein $R_6'$ comprises a leaving group Q preferably selected from the group consisting halo, sulfonyl or acyl substituted hydroxyl or amino;

(vi) coupling the compound of formula XIV″ with a compound of formula XVII

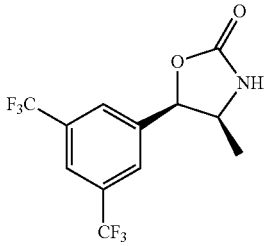
XVII in the presence of a base,
to yield a compound of formula DMAP,

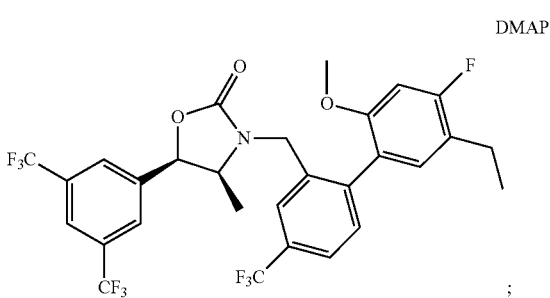 [SMILES: CCc1cc(-c2ccc(C(F)(F)F)cc2CN2C(=O)O[C@H](c3cc(C(F)(F)F)cc(C(F)(F)F)c3)[C@@H]2C)c(OC)cc1F]
DMAP

Optionally, compound of formula DMAP may be purified by re-precipitation in order to reduce level of other impurities.

The following examples further illustrate the invention. They are provided for illustrative purposes only and are not intended to limit the invention in any way. The examples and modifications or other equivalents thereof will become apparent to those versed in the art in the light of the present entire disclosure Experimental Procedures Comparative Example 1

Synthesis of Biphenyl XII″ According to Patent Application WO 2007/005572

Step 1: Synthesis of 2-(2-fluoro-4-methoxyphenyl)propan-2-ol (compound of formula 2, Scheme 3)

A commercially available 3M solution of MeMgCl (400 mL, 1.2 mol) in THF was cooled to −15° C., and a solution of 1-(2-fluoro-4-methoxyphenyl)ethanone (FMAP; cf. Scheme 3 above, compound of) (118 g, 0.7 mol) in dry THF (400 mL) was added dropwise, maintaining the internal temperature bellow 0° C. The reaction mixture was then aged at temperature −5 to 0° C. for an hour. The reaction was quenched with 2M HCl (700 mL) in a dropwise fashion maintaining, the internal temperature below 15° C. The quenched reaction was then aged at 10° C. for 1 hour and extracted with petroleum ether. The organic phase was then washed with water (2×700 mL) and the solvent removed under reduced pressure to yield compound 2 (FMOL) as a slightly bluish oil (121.8 g, 95%). $^1$H NMR (CDCl$_3$) δ 1.61 (d, J=1.0 Hz, 6H), 2.12 (bs, 1H), 3.78 (s, 3H), 6.61 (dd, J$_1$=20.6 Hz, J$_2$=2.7 Hz, 1H), 6.65 (dd, J$_1$=15.2 Hz, J$_2$=2.5 Hz, 1H), 7.43 (dd, J$_1$=9.5 Hz, J$_2$=8.7 Hz, 1H).

The product was contaminated with ~5% of the starting material compound 1 (FMOL). The reaction was repeated with CeCl$_3$ according to patent application WO 2007/005572. CeCl$_3$ should prevent enolization of starting material and thus should give a quantitative reaction yielding pure product FMOL without starting material FMAP. However, the results were even poorer regarding the remaining starting material 1 (FMOL) in the product 2 (FMAP) and also other impurities were detected.

Step 2: Synthesis of 2-fluoro-1-isopropyl-4-methoxybenzene (compound of formula 3, Scheme 3)

To a solution of compound of formula 2 of Scheme 3 (4.20 g, 25 mmol) in EtOH (30 mL), 37% HCl (2.2 mL, 27 mmol) diluted with EtOH (0.5 mL) was added, followed by 10% Pd/C (50% water) (66 mg, 0.5 mol %). The mixture was placed under 15 psi hydrogen at 40° C. until the reaction was complete based on HPLC analysis for an approximately 1 hour. The mixture was cooled to room temperature and the catalyst was removed by filtration. The solvent was removed under reduced pressure to a half of volume and water (10 mL) was added. The product of formula 3 was extracted into petroleum ether and the solvent removed under the reduced pressure to yield anisole of formula 3 as a colorless oil (4.14 g, 82%).
$^1$H NMR (CDCl$_3$) δ 1.22 (d, J=6.9 Hz, 6H), 3.15 (sept., J=6.9 Hz, 1H), 3.76 (s, 3H), 6.58 (dd, J$_1$=21.6 Hz, J$_2$=2.6 Hz, 1H), 6.62 (dd, J$_1$=15.2 Hz, J$_2$=2.5 Hz, 1H), 7.12 (t, J=8.7 Hz, 1H).

The impurity 1-ethyl-2-fluoro-4-methoxybenzene (MET) (~5%), which is formed from 1-(2-fluoro-4-methoxyphenyl)ethanone present in the starting material under the conditions described in Step 2, was detected in the product.

Step 3: Synthesis of 1-bromo-4-fluoro-5-isopropyl-2-methoxybenzene (compound of formula 4, Scheme 3)

2-fluoro-1-isopropyl-4-methoxybenzene (compound of formula 3, Scheme 3) (34.3 g, 0.204 mol) was dissolved in acetonitrile (400 mL). The solution was warmed to 35° C., and NBS (40 g, 0.225 mol) was added in a single solid addition. The reaction was maintained at 35° C. and was completed in 3-4 hours. The reaction was quenched with 2M Na$_2$SO$_3$ (40 mL, 0.08 mol). The resulting mixture was concentrated to ¼ of the total volume and diluted with water (400 mL) and petroleum ether (300 mL). The organic layer was cut and washed with water (300 mL), dried over Na$_2$SO$_4$ and filtered. The solvent was removed under reduced pressure to yield 1-bromo-4-fluoro-5-isopropyl-2-methoxybenzene (compound of formula 4, Scheme 3) as a slightly yellow oil (49.26 g, 98%). $^1$H NMR (CDCl$_3$) δ 1.22 (d, J=6.9 Hz, 6H), 3.14 (sept., J=6.9 Hz, 1H), 3.85 (s, 3H), 6.60 (d, J=11.8 Hz, 1H), 7.37 (d, J=8.0 Hz, 1H).

The impurity 1-bromo-5-ethyl-4-fluoro-2-methoxybenzene (BrMET) (~5%), which is formed from 1-ethyl-2-fluoro-4-methoxybenzene (MET) present in the starting material under the conditions described in Step 3, was detected in the product.

Step 4: Synthesis of 4-fluoro-5-isopropyl-2-methoxyphenylboronic acid (compound of formula 5, Scheme 3)

A 500 mL dry flask was charged with 2-bromo-5-fluoro-4-isopropylanisole (compound of formula 4, Scheme 3) (24.6 g, 0.1 mol) and dissolved in toluene (80 mL) and THF (80 mL). The resulting solution was flushed with argon, and tri-isopropylborate (32 mL, 0.14 mol) was added. The mixture was cooled to −80° C. Then 10 M n-BuLi in hexanes (12.5 mL, 0.125 mol) was added slowly, maintaining a temperature below −55° C. Thirty minutes after completion of the n-BuLi addition, the reaction was warmed to −35° C. and quenched into 3 M $H_2SO_4$ solution (75 mL, 0.225 mol). DIPE (200 mL) was added to the mixture to dilute the organic layer. The mixture was stirred (15 min) and the aqueous layer was cut away. The organic layer was washed with 3.0 M $H_2SO_4$ (75 mL). The organic phase was extracted three times with 1M NaOH (200 mL first and then 50 mL and 50 mL). The three NaOH extractions were combined, diluted with 2-propanol (85 mL), and cooled to 15° C. Then the solution was slowly acidified to pH ~2 using 3 M $H_2SO_4$ (70 mL) while maintaining temperature at 15-20° C. The resulting slurry was stirred for 1 hour and then filtered. The filter cake was washed with water (3×30 mL) and dried under an air flow for 1 day. The white crystalline solid was isolated to yield boronic acid of formula 5 (Scheme 3) (19.23 g, 91%): mp 100-102° C.; $^1$H NMR ($CDCl_3$) δ 1.25 (d, J=6.9 Hz, 6H), 3.17 (sept., J=6.9 Hz, 1H), 3.88 (s, 3H), 5.83 (s, 2H), 6.59 (d, J=12.4 Hz, 1H), 7.72 (d, J=6.6 Hz, 1H).

The impurity 5-ethyl-4-fluoro-2-methoxyphenylboronic acid (~4%), which is formed from 1-bromo-5-ethyl-4-fluoro-2-methoxybenzene (BrMET) present in the starting material under the conditions described in Step 4, was detected in the product.

Step 5 (Suzuki reaction): Synthesis of (4'-fluoro-5'-isopropyl-2'-methoxy-4-(trifluoromethyl)biphenyl-2-yl)methanol (compound of formula 6, Scheme 3)

A 3 M $K_2CO_3$ solution is prepared by adding solid $K_2CO_3$ (31 g, 0.22 mol) to water (100 mL). Cooling is applied to keep the solution at 20-25° C. (2-chloro-5-(trifluoromethyl)phenyl) methanol (compound of formula 13) (17.5 g, 84 mmol), and boronic acid 5 (Scheme 3) (18.1 g, 85 mmol) are added to the $K_2CO_3$ followed by THF (100 mL) rinse. The solution is degassed by sparging with argon gas for 20 min. The catalyst, 1,1 bis(di-tert-butylphosphino)ferrocene palladium dichloride (300 mg, 0.55 mol %) is added. The organic layer turns dark brown immediately. The biphasic mixture is aged at 35-45° C. with vigorous stirring for 32 hours. The mixture is cooled to room temperature and water (150 mL) is added, followed by petroleum ether (150 mL) and the aqueous layer is removed. The organic layer was washed with water (2×200 mL) and filtered through silica gel and the solvent is removed under reduced pressure to yield brownish oil which is crystallized from heptane to give a pale white solid (28.5 g, 80%). mp 93.5-95.5° C.; $^1$H NMR ($CDCl_3$) δ 1.24 (d, J=6.9 Hz, 6H), 1.95 (t, J=6.1 Hz, 1H), 3.21 (sept., J=6.9 Hz, 1H), 3.73 (s, 3H), 4.49 (m, 2H), 6.68 (d, J=12.0 Hz, 1H), 6.99 (d, J=8.6 Hz, 1H), 7.30 (d, J=7.9 Hz, 1H), 7.59 (dd, $J_1$=8.0 Hz, $J_2$=1.3 Hz, 1H), 7.86 (d, J=0.7 Hz, 1H).

The impurity (5'-ethyl-4'-fluoro-2'-methoxy-4-(trifluoromethyl)biphenyl-2-yl)methanol (~3%), which is formed from 5-ethyl-4-fluoro-2-methoxyphenylboronic acid present in the starting material under the conditions described in Step 5, was detected in the product.

Step 6: Synthesis of 2'-(chloromethyl)-4-fluoro-5-isopropyl-2-methoxy-4'-(trifluoromethyl)biphenyl (compound of formula 7, Scheme 3)

To a solution of biaryl compound 6 (Scheme 3) (28.5 g, ~75 mmol) in DMF (140 mL) which was maintained at 10° C. was added thionyl chloride (7.3 mL, 100 mmol), and then the mixture was warmed to room temperature. The mixture was aged for 5 hours and water (200 mL) was then added. The crystallization described in the prior art from DMF/water could not be repeated so that is why the product was extracted with petroleum ether (150 mL). The organic phase was washed with water (3×150 mL) and the solvent removed under reduced pressure to obtain a brown oil (29.2 g) which was then crystallized from MeOH (60 mL). The solid was filtered and washed with ice cold MeOH (20 mL) to yield a compound of formula 6 (Scheme 3) as colorless crystals (20.95 g, 78% for two steps): mp 45-49° C.; $^1$H NMR ($CDCl_3$) δ 1.25 (d, J=6.9 Hz, 6H), 3.22 (sept., J=6.9 Hz, 1H), 3.72 (s, 3H), 4.43 (dd, $J_1$=34.6 Hz, $J_2$=10.0 Hz, 2H), 6.68 (d, J=12.0 Hz, 1H), 7.08 (d, J=8.6 Hz, 1H), 7.33 (d, J=8.0 Hz, 1H), 7.60 (dd, $J_1$=8.0 Hz, $J_2$=1.3 Hz, 1H), 7.83 (d, J=0.7 Hz, 1H).

The impurity 2'-(chloromethyl)-5-ethyl-4-fluoro-2-methoxy-4'-(trifluoromethyl)biphenyl (EBFCI) (~3%), which is formed from (5'-ethyl-4'-fluoro-2'-methoxy-4-(trifluoromethyl)biphenyl-2-yl)methanol present in the starting material under the conditions described in Step 6, was detected in the product.

Step 7: Synthesis of (4S,5R)-5-[3,5-bis(trifluoromethyl)phenyl]-3-[[2-(4-fluoro-2-methoxy-5-propan-2-ylphenyl)-5-(trifluoromethyl)phenyl]methyl]-4-methyl-1,3-oxazolidin-2-one (anacetrapib)

The chiral intermediate (4S,5R)-5-(3,5-bis(trifluoromethyl)phenyl)-4-methyloxazolidin-2-one (compound of formula XV; cf. also compound 11 in Scheme 3) (28.0 g) prepared by the procedure of WO 2007/005572 is dissolved in DMF (300 mL) and cooled to −15° C. 2 M NaHMDS (39.2 mL, 1.05 eq) was then added over 1 h, followed by addition of the biaryl chloride 7 (Scheme 3) (28.0 g) in DMF (50 mL), maintaining the internal temperature below −10° C. The mixture was warmed to +12° C. and was aged until complete conversion took place. Then 5M HCl (35 mL) was added, followed by 160 mL of 10% IPAC/Heptanes and 340 mL of water, keeping the temperature between 10° C. and 20° C. throughout. The layers were cut and the organic layer was washed twice with 150 mL of 1/1 DMF/water followed by two 140 mL water washes. The organic layer was then removed under reduced pressure and the resulting residue was purified by flash chromatography (EtOAc/hexanes) to remove the excess oxazolidinone 11 (Scheme 3). The obtained colorless oil was then dissolved in refluxing heptanes (200 mL) and the solution was slowly cooled to −20° C. The resulting slurry was then stirred at −20° C. for 2 hours and filtered. The filter cake was washed with cold heptanes and was then dried, yielding 44.0 g (88%) of the desired product of compound of formula XV" (anacetrapib) as an amorphous material.

An impurity of compound of formula XVII" (4S,5R)-5-(3,5-bis(trifluoromethyl)phenyl)-3-((5'-ethyl-4'-fluoro-2'-methoxy-4-(trifluoromethyl) biphenyl-2-yl)methyl)-4-methyloxazolidin-2-one (DMAP) is present in the thus obtained anacetrapib in an amount of about 3% by weight relative to the total amount of anacetrapib product. DMAP originates from 2'-(chloromethyl)-5-ethyl-4-fluoro-2-methoxy-4'-(trifluoromethyl)biphenyl (EBFCI) representing an impurity which forms in the preparation path of 2'-(chloromethyl)-4-fluoro-5-isopropyl-2-methoxy-4'-(trifluoromethyl)biphenyl under the above described conditions.

Example 1

Synthesis of Desmethyl Impurity (DMAP)

Step 1: Synthesis of 2-fluoro-1-isopropyl-4-methoxybenzene (MET)

To a solution of 1-(2-fluoro-4-methoxyphenyl)ethanone (FMAP) (13.46 g, 80 mmol) in MeOH (100 mL), 37% HCl (7.0 mL, 85 mmol) diluted with MeOH (5 mL) was added, followed by 5% Pd/C (340 mg, 0.4 mol %). The mixture was placed under 3 bar hydrogen at rt until the reaction was complete based on HPLC analysis. The mixture was cooled to room temperature and the catalyst was removed by filtration. The solvent was removed under reduced pressure, and water (100 mL) and petroleum ether were added. The organic layer was cut and washed with water (50 mL) and dried over $Na_2SO_4$. The solvent was removed under the reduced pressure. The oily residue was distilled using 8×1 cm distillation column with Raschig rings at 95-97° C. and 45 mbar to yield 1-ethyl-2-fluoro-4-methoxybenzene (MET) as a colorless oil (8.15 g, 66%): $^1$H NMR (CDCl$_3$) δ 1.19 (t, J=7.6, 3H), 2.60 (q, J=7.6, 2H), 3.77 (s, 3H), 6.52-6.68 (m, 2H), 7.08 (t, J=8.6, 1H).

Step 2: synthesis of 1-bromo-5-ethyl-4-fluoro-2-methoxybenzene (BrMET)

1-ethyl-2-fluoro-4-methoxybenzene (MET) (7.70 g, 50 mmol) was dissolved in acetonitrile (100 mL), and NBS (9.80 g, 55 mmol) was added in a single solid addition. The reaction was stirred at rt and was completed in 3-4 hours. The reaction mixture was quenched with 2M $Na_2SO_3$ (40 mL, 0.08 mol) and concentrated to ¼ of the total volume, then diluted with water (80 mL) and petroleum ether (50 mL). The organic layer was cut and washed with water (3×50 mL), 1M NaOH (50 mL), water (50 mL), dried over $Na_2SO_4$ and filtered. The solvent was removed under reduced pressure to yield 1-bromo-5-ethyl-4-fluoro-2-methoxybenzene (BrMET) as a colorless oil (11.16 g, 96%): $^1$H NMR (CDCl$_3$) δ 1.19 (t, J=7.6, 3H), 2.58 (q, J=7.6, 2H), 3.85 (s, 3H), 6.61 (d, J=11.4, 1H), 7.35 (d, J=8.1, 1H).

Step 3: Synthesis of 5-ethyl-4-fluoro-2-methoxyphenylboronic acid (METB)

A dry flask was charged with 1-bromo-5-ethyl-4-fluoro-2-methoxybenzene (BrMET) (7.00 g, 30 mmol) and tri-isopropylborate (9.6 mL, 42 mol), and toluene (20 mL) and THF (20 mL) were added. The resulting solution was flushed with argon and cooled to −80° C. Then 10 M n-BuLi in hexanes (3.8 mL, 38 mmol) was added slowly, maintaining a temperature below −55° C. Thirty minutes after completion of the n-BuLi addition, the reaction was allowed to warm up to −30° C. (2 hours) and then quenched into 1 M $H_2SO_4$ (aq) (50 mL). DIPE (80 mL) was added to the mixture to dilute the organic layer. The mixture was stirred (15 min) and the aqueous layer was cut away. The organic layer was washed with 1 M $H_2SO_4$ (50 mL). The organic phase was extracted three times with 1 M NaOH (40 mL first and then 2×10 mL). The three NaOH extractions were combined, diluted with 2-propanol (10 mL), and cooled to 15° C. Then the solution was slowly acidified to pH ~2 using 3 M $H_2SO_4$ (10 mL) while maintaining temperature at 15-20° C. The resulting slurry was stirred for 1 hour and then filtered. The filter cake was washed with water (3×15 mL) and dried under an air flow for 1 day. The filtered solid was placed in an oven under vacuum at 50° C. for 2-3 days to decompose a diaryl impurity and to dry the solid. The off-white crystalline solid was isolated to yield boronic acid METB (3.40 g, 57%): $^1$H NMR (CDCl$_3$) δ 1.23 (t, J=7.6, 3H), 2.64 (q, J=7.6, 2H), 3.90 (s, 3H), 6.04 (s, 2H), 6.62 (d, J=12.0, 1H), 7.70 (d, J=9.7, 1H).

Step 4: Synthesis of (5'-ethyl-4'-fluoro-2'-methoxy-4-(trifluoromethyl)biphenyl-2-yl)methanol (EBFOH)

$K_2CO_3$ (3.32 g, 24 mmol) is dissolved in water (20 mL) and the resulting solution is degassed by sparging with argon gas for 10 min. (2-chloro-5-(trifluoromethyl)phenyl) methanol (COK) (2.94 g, 14 mmol), and boronic acid METB (2.78 g, 14 mmol) dissolved in THF (20 mL) are added to the $K_2CO_3$ solution. The resulting solution is degassed by sparging with argon gas for 15 min. The catalyst, 1,1 bis(di-tertbutylphosphino)ferrocene palladium dichloride (75 mg, 0.8 mol %) is added. The organic layer turns dark brown immediately. The biphasic mixture is aged at 35° C. with vigorous stirring for 24 hours. The mixture is cooled to rt and water (80) is added, followed by DIPE (80 mL) and the aqueous layer is removed. The organic layer was washed with 1 M NaOH (aq) (50 mL), 1 M HCl (aq) (50 mL) and water (50 mL), dried over $Na_2SO_4$, and filtered through silica gel pot. The solvent is removed under reduced pressure to yield EBFOH as a brownish solid (4.18 g, 91%): $^1$H NMR (CDCl$_3$) δ 1.22 (t, J=7.6, 3H), 1.95 (t, J=6.2, 1H), 2.64 (q, J=7.5, 2H), 4.49 (bs, 2H), 6.69 (d, J=11.6, 1H), 6.96 (d, J=8.7, 1H), 7.29 (d, J=7.9, 1H), 7.58 (d, J=7.9, 1H), 7.85 (s, 1H).

Step 5: Synthesis of 2'-(chloromethyl)-5-ethyl-4-fluoro-2-methoxy-4'-(trifluoromethyl)biphenyl (EBFCI)

To a solution of biaryl compound EBFOH (2.99 g, 9.1 mmol) in DMF (15 mL) which was maintained at 10° C. was added thionyl chloride (0.73 mL, 10 mmol), and then the mixture was warmed to room temperature. The mixture was aged for 5 hours and water (20 mL) was then added, followed by petroleum ether (20 mL). The organic layer was cut away and washed with water (3×20 mL). The solvent was removed under reduced pressure to obtain a brown oil (3.20 g) which was then crystallized from MeOH (6 mL). The solid was filtered and washed with ice cold MeOH (2 mL) to yield EBFCI as colorless crystals (2.52 g, 80%). $^1$H NMR (CDCl$_3$) δ 1.22 (t, J=7.5, 3H), 2.65 (q, J=7.5, 2H), 3.72 (s, 3H), 4.43 (dd, $J_1$=32.4, $J_2$=10.5, 2H), 6.68 (d, J=11.7, 1H), 7.03 (d, J=8.6, 1H),

Step 6: Synthesis of (4S,5R)-5-(3,5-bis(trifluoromethyl)phenyl)-3-((5'-ethyl-4'-fluoro-2'-methoxy-4-(trifluoromethyl)biphenyl-2-yl)methyl)-4-methyloxazolidin-2-one (desmethylanacetrapib, DMAP)

The chiral intermediate (4S,5R)-5-(3,5-bis(trifluoromethyl)phenyl)-4-methyloxazolidin-2-one (compound of formula XV; cf. also compound 11 in Scheme 3) (280 mg) prepared by procedure of WO 2007/005572 is dissolved in DMF (30 mL) and cooled to −15° C. 2 M NaHMDS (3.90 mL, 1.05 eq) was then added over 1 h, followed by addition of the biaryl chloride EBFCI (270 mg) in DMF (5 mL), maintaining the internal temperature below −10° C. The mixture was warmed to +12° C. and was aged until complete conversion took place. Then 5M HCl (3.5 mL) was added, followed by 20 mL of 10% IPAC/Heptanes and 40 mL of water, keeping the temperature between 10° C. and 20° C. throughout. The layers were cut and the organic layer was washed twice with 20 mL of 1/1 DMF/water followed by two 15 mL water washes. The organic layer was then removed under reduced pressure and the resulting residue was purified by flash chromatography (EtOAc/hexanes) to remove the excess oxazolidinone (compound of formula XV). The pure (4S,5R)-5-(3,5-bis(trifluoromethyl)phenyl)-3-((5'-ethyl-4'-fluoro-2'-methoxy-4-(trifluoromethyl)biphenyl-2-yl)methyl)-4-methyloxazolidin-2-one (DMAP, compound of formula XII") was obtained as a colorless oil (388 mg, 80%).

Example 2

Methylation of 2'-fluoro-4'-methoxyacetophenone (FMAP) by Grignard Reaction 3M solution of MeMgCl in THF, optionally with anhydrous cerium (III) chloride and a solution 2'-fluoro-4'-methoxyacetophenone in a selected solvent are mixed together by various manners, maintaining the internal temperature, below 0° C. and reaction is quenched by MeOH and then with 2M HCl. The resulted solution is analyzed to FMOL/FMAP ration. Addition protocol and results of reaction are listed in Table 1.

TABLE 1

| | | FMOL:FMAP mol % ratio by $^1$H-NMR | |
|---|---|---|---|
| | Experiment | FMOL | FMAP |
| Adding Grignard reagent to ketone FMAP | Adding 20 mmol MeMgCl/THF (3M) to a solution of 10 mmol FMAP in 20 mL THF (experiment according to the present invention) | 88 | 12 |
| | Adding 20 mmol MeMgCl/THF (3M) to a solution of 10 mmol FMAP in 20 mL DCM (experiment according to the present invention) | 99.9 | 0.1 |
| Adding ketone FMAP to Grignard reagent | Adding 10 mmol FMAP in 5 mL THF to a solution of 14 mmol MeCeCl$_2$ in 30 mL THF at T ≤ 0° C. (experiment according to the present invention) | 84 | 16 |
| | Adding 10 mmol FMAP in 5 mL THF to a solution of 7 mmol Me$_2$CeCl in 30 mL THF at T ≤ 0° C. (experiment according to pat. appl. WO 2007/005572) | 93 | 7 |
| | Adding 0.7 mol FMAP in 400 mL THF to a solution of of 1.2 mol MeMgCl/THF (3M) at T ≤ 0° C. (experiment according to pat. appl. WO 2007/005572 without using CeCl$_3$ - see Example 1, Step 1) | 94 | 6 |
| | Adding 10 mmol FMAP in 20 mL methyl tert-butyl ether to a solution of 15 mmol MeMgCl/THF (3M) (experiment according to the present invention) | 93 | 7 |
| | Adding 10 mmol FMAP in 20 mL diethyl ether to a solution of 15 mmol MeMgCl/THF (3M) (experiment according to the present invention) | 93 | 7 |
| | Adding 10 mmol FMAP in 20 mL 1,4-dioxane to a solution of 15 mmol MeMgCl/THF (3M) (experiment according to the present invention) | 85 | 15 |

TABLE 1-continued

| | | FMOL:FMAP mol % ratio by $^1$H-NMR | |
|---|---|---|---|
| | Experiment | FMOL | FMAP |
| | Adding 10 mmol FMAP in 20 mL 1,2-dimethoxyethane to a solution of 15 mmol MeMgCl/THF (3M) (experiment according to the present invention) | 99.9 | 0.1 |
| | Adding 0.30 mol FMAP in 230 mL DCM to a solution of 0.45 mmol MeMgCl/THF (3M) (experiment according to the present invention) | 99.9 | 0.1 |
| | Adding 0.30 mol FMAP in 230 mL toluene to a solution of 0.45 mmol MeMgCl/THF (3M) (experiment according to the present invention) | 99.9 | 0.1 |

In conclusion, chemoselectivity of Grignard reaction is significantly increased in case a second solvent such as e.g. dichloromethane, toluene or 1,2-dimethoxyethane is present in the reaction mixture besides of a first solvent such as e.g. THF, which is a typical solvent for commercial Grignard reagents, and thus, the obtained product FMOL was substantially free of starting material FMAP.

Example 2B

Converting BrFMAP to BrFMOL

A 1 L round bottom flask equipped with an magnetic stirrer, an argon inlet and a temperature probe was charged with the commercially available 3M solution of MeMgCl (100 mL, 0.30 mol) in THF. The solution was cooled to −10° C., and a solution of acetophenone BrFMAP (57.00 g, 0.23 mol) in dry DCM (200 mL) was added dropwise, maintaining the internal temperature below 0° C. The reaction mixture was then aged at temperature 0° C. for 2 hours and the reaction mixture was quenched first with MeOH (25 mL) and then with 1M HCl (250 mL), maintaining the internal temperature below 20° C. The quenched reaction was then aged at 20° C. for 30 min and the layers were cut. The organic phase was washed with water (300 mL) and brine (200 mL). The solvent was removed under reduced pressure to yield BrFMOL as a colorless oil (60.10, 99%), which solidifies upon standing.

The product BrFMOL was substantially free of desmethyl impurity, preferably free of BrFMAP as determined by NMR and HPLC.

According to the same procedure in various scales, the product, substantially free of desmethyl impurity, is also prepared in toluene and 1,2-dimethoxyethane.

Example 3

Preparation of 2-(2-fluoro-4-methoxy)phenylpropanol (FMOL)

A 2 L round bottom flask equipped with an magnetic stirrer, an argon inlet and a temperature probe was charged with the commercially available 3M solution of MeMgCl (600 mL, 1.80 mol) in THF. The solution was cooled to −10° C., and a solution of acetophenone FMAP (170 g, 1.01 mol) in dry DCM (800 mL) was added dropwise, maintaining the internal temperature below 0° C. The reaction mixture was then aged at temperature 0° C. for 2 hours and the reaction mixture was divided to three parts.

Quenching 1

One third of mixture was quenched first with MeOH (25 mL) and then with 2M HCl (250 mL) in a dropwise fashion, maintaining the internal temperature below 20° C. The quenched reaction was then aged at 20° C. for 30 min and the layers were cut. The organic phase was washed with water (300 mL) and brine (200 mL). The solvent was removed under reduced pressure to yield FMOL as colorless oil (61.5 g, 99%). The product was analyzed on assay of FMOL and MIPEN (Table 2). The NMR and HPLC showed that starting material FMAP was present only in traces (~0.1%).

Quenching 2

One third of mixture was quenched first with chloroform (30 mL) and then with water (200 ml) in a dropwise fashion, maintaining the internal temperature below 15° C. The quenched reaction was then aged at 20° C. for 30 min and the layers were cut. The organic phase was washed with water (300 mL) and brine (200 mL). The solvent was removed under reduced pressure to yield FMOL as colorless oil (61.5 g, 99%). The product was analyzed on assay of FMOL and MIPEN (Table 2). The NMR and HPLC showed that starting material FMAP was present only in traces (~0.1%).

Quenching 3

One third of mixture was quenched with 2M HCl (aq) (125 mL) in a dropwise fashion, maintaining the internal temperature below 20° C. (Caution: very exothermic). The quenched reaction was then aged at 20° C. for 1 hour and the layers were cut. The organic phase was washed with water (250 mL) and brine (200 mL). The solvent was removed under reduced pressure to yield FMOL as colorless oil (57.8 g, 97% calculated to the average MW). The product was analyzed on assay of FMOL and MIPEN (Table 2). The NMR and HPLC showed that starting material FMAP was present only in traces (~0.1%).

The ratio between FMOL and its dehydrated analogue MIPEN depends on the quenching process and temperature as shown in Table 2 below.

TABLE 2

| Quenching process | Ratio (mol %)* | |
| --- | --- | --- |
|  | FMOL | MIPEN |
| Example 4, Quenching 1 | 99.6 | 0.4 |
| Example 4, Quenching 2 | 99.8 | 0.2 |
| Example 4, Quenching 3 | 45.5 | 54.5 |

*Note:
ratio determined by comparison of integrals in $^1$H-NMR

Example 4

One pot preparation of 1-bromo-4-fluoro-5-isopropyl-2-methoxybenzene (BrMIP)

A 2 L round bottom flask equipped with an magnetic stirrer, an argon inlet and a temperature probe was charged with the commercially available 3M solution of MeMgCl (600 mL, 1.80 mol) in THF. The solution was cooled to −10° C., and a solution of acetophenone FMAP (170 g, 1.01 mol) in dry DCM (800 mL) was added dropwise, maintaining the internal temperature below 0° C. The reaction mixture was then aged at temperature 0° C. for 2 hours. The reaction was quenched with 2M HCl (aq) (900 mL) in a dropwise fashion, maintaining the internal temperature below 20° C. (Caution: very exothermic). The quenched reaction was then aged at 20° C. for 1 hour and the layers were cut. The organic phase was washed with water (1000 mL) and brine (800 mL) and was concentrated under reduced pressure to 220 g. The concentrate contains FMOL and MIPEN in ratio 5:6 estimated by $^1$HNMR with total assay of both products ~0.97 mol).

The NMR and HPLC showed that the obtained product was substantially free of starting material FMAP, analyzed by HPLC and NMR using identification standard, prepared according to Example 2.

A part of above concentrate (94 mL, 73 g of total FMOL/MIPEN, ~0.42 mol) was diluted with MeOH, purged with $N_2$ and 5% Pd—C (1.70 g, 0.2 mol %) was added. The mixture was purged with hydrogen and placed under 3 bar at 50° C. until the reaction was complete based on HPLC analysis. The catalyst was removed by filtration through Celite®. The obtained solution was transferred to a new flask and 1,3-dibromo-5,5-dimethylhydantoin (60.7 g, 208 mmol) was added in portions, maintaining the temperature below 40° C. (Caution: exothermic reaction). Eight hours after the completion of the 3-dibromo-5,5-dimethylhydantoin addition, the reaction was complete by HPLC. The reaction was quenched with $NaHSO_3$ (5.0 g) and mixed for another 15 minutes. The solution was concentrated to ⅕ of volume and diluted with water (500 mL). The resulting mixture was extracted with petroleum ether (300 mL) and then the organic phase was washed with water (500 mL), 1M NaOH (aq) (250 mL), water (500 mL) and brine (200 mL). The organic phase was dried over $Na_2SO_4$, filtered and the solvent removed under reduce pressure to yield BrMIP as a slightly yellow oil (93.03 g, 91% according to FMAP). $^1$H NMR (CDCl$_3$) δ 1.22 (d, J=6.9 Hz, 6H, 2×Me), 3.14 (sept., J=6.9 Hz, 1H), 3.85 (s, 3H), 6.60 (d, J=11.8 Hz, 1H), 7.37 (d, J=8.0 Hz, 1H).

The product BrMIP was substantially free of desmethyl impurity BrMET, analyzed by HPLC and NMR using identification standard, prepared according to Example 2.

Example 5

Preparation of 4-fluoro-5-isopropyl-2-methoxyphenylboronic acid (MIPB) from BrMIP A 2 L dry flask was charged with BrMIP (98.4 g, 0.4 mol) and dissolved in toluene (320 mL) and THF (320 mL). The resulting solution was flushed with argon, and triisopropyl borate (128 mL, 0.56 mol) was added. The mixture was cooled to −80° C. Then 10 M n-BuLi in hexanes (50 mL, 0.5 mol) was added slowly, maintaining a temperature below −55° C. Thirty minutes after completion of the n-BuLi addition, the reaction was warmed to −35° C. and quenched into 3 M $H_2SO_4$ solution (300 mL, 0.9 mol). DIPE (800 mL) was added to the mixture to dilute the organic layer. The mixture was stirred (15 min) and the aqueous layer was cut away. The organic layer was washed with 3.0 M $H_2SO_4$ (75 mL). The organic phase was extracted three times with 1M NaOH (800 mL first and then twice with 200 mL). The three NaOH extractions were combined, diluted with 2-propanol (340 mL), and cooled to 15° C. Then the solution was slowly acidified to pH ~2 using 3 M $H_2SO_4$ (280 mL) while maintaining temperature at 15-20° C. The resulting slurry was stirred for 1 hour and then filtered. The filter cake was washed with water (3×90 mL) and dried under an air flow for 1 day. The off-white crystalline solid was isolated to yield MIPB (77.0 g, 91%). mp 100-102° C.; $^1$H NMR (CDCl$_3$) δ 1.25 (d, J=6.9 Hz, 6H), 3.17 (sept., J=6.9 Hz, 1H), 3.88 (s, 3H), 5.83 (s, 2H), 6.59 (d, J=12.4 Hz, 1H), 7.72 (d, J=6.6 Hz, 1H).

The product MIPB was substantially free of desmethyl impurity METB, analyzed by HPLC and NMR using identification standard, prepared according to Example 2.

Example 6

Preparation of Boronic Acid MIPB Via Grignard Intermediate MgBrMIP

A dry flask was purged with argon and charged with THF (150 mL), Mg powder (2.5 g, 100 mmol), a few crystals of iodine and 1,2 dibromoethane (1 mL). The mixture was sonicated until the disappearance of iodine color and then a solution of BrMIP (12.40 g, 50 mmol) in THF (50 mL) was added dropwise. The resulting mixture was sonicated until the reaction was complete based on HPLC analysis (1 hour). The excess of magnesium was removed by filtration and the resulting solution of MgBrMIP (0.25 M) was added to the solution of trimethyl borate (11.50 mL, 100 mmol) in toluene (140 ml), maintaining the temperature at 5° C. The resulting mixture was stirred for 2 hours at 10° C., quenched by 1 M $H_2SO_4$ (50 mL) and water was added (250 mL). The water layer was cut away and the organic phase was extracted three times with 1M NaOH (50 mL first and then twice with 20 mL). The three NaOH extractions were combined, diluted with 2-propanol (30 mL), and cooled to 15° C. Then the solution was slowly acidified to pH ~2 using 3 M $H_2SO_4$ maintaining temperature at 15-20° C. The resulting slurry was stirred for 1 hour and then filtered. The filter cake was washed with water (3×50 mL) and dried under vacuum 1 day. The off-white crystalline solid was isolated to yield MIPB (8.70 g, 82%). mp 100-102° C.; $^1$H NMR (CDCl$_3$) δ 1.25 (d, J=6.9 Hz, 6H), 3.17 (sept., J=6.9 Hz, 1H), 3.88 (s, 3H), 5.83 (s, 2H), 6.59 (d, J=12.4 Hz, 1H), 7.72 (d, J=6.6 Hz, 1H).

The product MIPB was substantially free of desmethyl impurity METB, analyzed by HPLC and NMR using identification standard, prepared according to Example 2.

Example 7

Synthesis of (4'-fluoro-5'-isopropyl-2'-methoxy-4-(trifluoromethyl)biphenyl-2-yl)methanol (Formula XII', $R_6$=CH$_2$OH)

A 3 M K$_2$CO$_3$ solution is prepared by adding solid K$_2$CO$_3$ (31 g, 0.22 mol) to water (100 mL). (2-chloro-5-(trifluoromethyl)phenyl) methanol (17.5 g, 84 mmol), and MIPB (18.1 g, 85 mmol) are added to the K$_2$CO$_3$ followed by all THF (100 mL) rinse. The solution is degassed by sparging with argon gas for 20 min. The catalyst, 1,1-bis(di-tertbutylphosphino) ferrocene palladium dichloride (300 mg, 0.55 mol %) is added. The organic layer turns dark brown immediately. The biphasic mixture is aged at 35-45° C. with vigorous stirring for 32 hours. The mixture is cooled to r. t. and water (150 mL) is added, followed by petroleum ether (150 mL) and the aqueous layer is removed. The organic layer was washed with water (2×200 mL) and filtered through silica gel and the solvent is removed under reduced pressure to yield brownish oil which is crystallized from heptane to give a pale white solid (28.5 g, 80% calculated on the pure product). mp 93.5-95.5° C.; $^1$H NMR (CDCl$_3$) δ 1.24 (d, J=6.9, 6H), 1.95 (t, J=6.1, 1 H), 3.21 (sept., J=6.9, 1 H), 3.73 (s, 3H), 4.49 (m, 2H), 6.68 (d, J=12.0, 1 H), 6.99 (d, J=8.6, 1H), 7.30 (d, J=7.9 Hz, 1H), 7.59 (dd, J, =8.0, J$_2$=1.3, 1H), 7.86 (d, J=0.7, 1H).

The product BFOH was substantially free of desmethyl impurity EBFOH, analyzed by HPLC and NMR using identification standard, prepared according to Example 2.

According to the same procedure as described above, experiments with other biaryls of compound of formula XII' different scales and/or different catalyst concentrations have been carried out. The results of these experiments are listed in Table 3

TABLE 3

| XI (scale) | XII ($R_6$) | Pd-cat (mol %) | Crystallization | Yield (%)* | $^1$HNMR | Mp (° C.) |
|---|---|---|---|---|---|---|
| 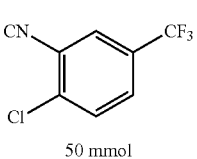 50 mmol | 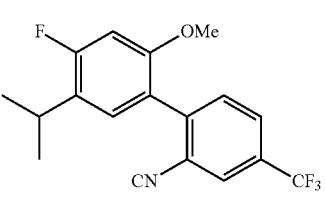 $R_6$ = CN | (A) 0.9 | MeOH/water | 40 | $^1$H NMR (CDCl$_3$) δ 1.27 (d, J = 6.9, 6H), 3.22 (sept., J = 6.9, 1H), 3.81 (s, 3H), 6.73 (d, J = 12.0, 1H), 7.13 (d, J = 8.4, 1H), 7.60 (d, J = 8.2, 1H), 7.85 (ddd, J = 8.1, 1.9, 0.5, 1H), 7.97 (s, 1H) | 60-72 |
| 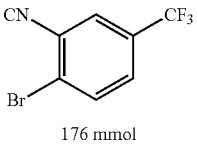 176 mmol | 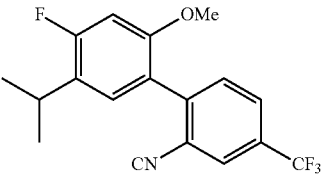 $R_6$ = CN | (A) 0.5 | MeOH/water | 81 | | |

TABLE 3-continued

| XI (scale) | XII (R$_6$) | Pd-cat (mol %) | Crystallization | Yield (%)* | $^1$HNMR | Mp (°C.) |
|---|---|---|---|---|---|---|
| 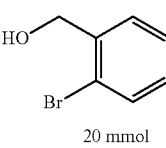 20 mmol | 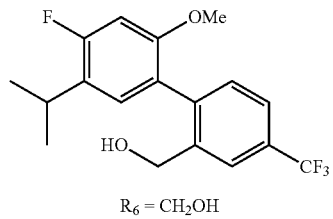 R$_6$ = CH$_2$OH | (A) 0.6 | hexanes | 82 | $^1$H NMR (CDCl$_3$) δ 1.24 (d, J = 6.9, 6H), 1.95 (t, J = 6.1, 1H), 3.21 (sept., J = 6.9, 1H), 3.73 (s, 3H), 4.49 (m, 2H), 6.68 (d, J = 12.0, 1H), 6.99 (d, J = 8.6, 1H, ArH), 7.30 (d, J = 7.9, 1H, ArH), 7.59 (dd, J = 8.0, 1.3, 1H, ArH), 7.86 (d, J = 0.7, 1H, ArH) | 93-95 |
| 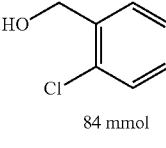 84 mmol | 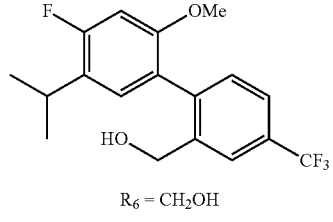 R$_6$ = CH$_2$OH | (A) 0.6 | hexanes | 80 | | |
| 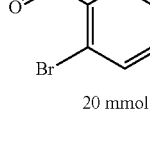 20 mmol | 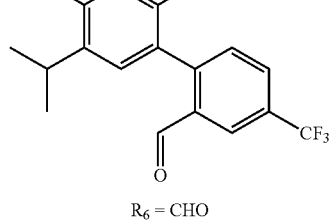 R$_6$ = CHO | (B) 1 | MeOH/water | 95 | $^1$H NMR (CDCl$_3$) δ 1.27 (d, J = 6.9, 6H), 3.23 (sept., J = 6.9, 1H), 3.72 (s, 3H), 6.69 (d, J = 11.9, 1H), 7.13 (d, J = 8.4, 1H), 7.47 (d, J = 8.0, 1H), 7.86 (ddd, J = 8.1, 2.0, 0.5,, 1H), 8.24 (m, 1H), 9.77 (s, 1H) | 42-48 |
| 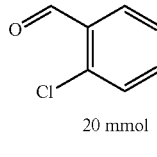 20 mmol | 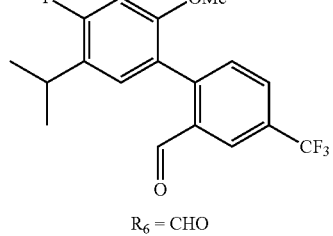 R$_6$ = CHO | (B) 1 | MeOH/water | 90 | | |

Note:
(A): Pd-catalyst was 1,1 bis(di-tertbutylphosphino)ferrocene palladium dichloride at room temperature
(B): Pd-catalyst was Pd(OAc)$_2$ (1 mol %) with PPh$_3$ (4 mol %) at 50° C.
*Yield after crystallization, turnover of the reactions was higher

Example 8

Preparation of biaryl of Formula XII' (R$_6$=COOH)

Outside the glovebox, a 100 mL Schlenk flask equipped with a magnetic stir bar was charged with commercially available 3-(trifluoromethyl)benzoic acid (BFA) (3.09 g, 16.2 mmol) and bromoanisole BrMIP (3.60 g, 14.6 mmol). The flask was transferred to glovebox (% O$_2$≤0.005) and Pd(OAc)$_2$ (157 mg, 5 mol %), n-butyl-di-1-adamantylphosphine (530 mg, 10 mol %), Cs$_2$CO$_3$ (11.92 g, 36.6 mmol) and powdered dry molecular sieves 3 Å (1.0 g) were added. The flask was closed with the rubber septum and taken out of the glovebox. Anhydrous DMF degassed with nitrogen was added through the septum and the obtained mixture was first stirred at room temperature for 1 h under the positive pressure of nitrogen, and then placed in a preheated oil bath (145° C.) for 24 h. The reaction mixture was cooled to room temperature and quenched with 2M HCl (100 mL). Ethylacetate (50 mL) was added and the resulting suspension was stirred for 15 min, filtered through a pad of celite and the layers were cut. The water layer was extracted with ethyl acetate (50 mL) and all organic phases were combined, washed with brine (50 mL) and evaporated under reduced pressure to obtain a yellow oil. The crude product was purified by column chromatography to give 4'-fluoro-5'-isopropyl-Z-methoxy-4-(trifluoromethyl)biphenyl-2-carboxylic acid as a colorless oil (3.11 g, 60%). $^1$H NMR (DMSO-d$_6$) δ 0.95 (d, J=8.0, 6H), 3.36 (s, 1H), 6.26 (d, J=12.0, 1H), 6.83 (d, J=8.0, 1H), 7.03 (d, J=8.0, 1 H), 7.25 (m, 1H), 7.74 (s, 1H).

Example 9

Preparation of biaryls of Formula XII' ($R_6$=$CH_2OCH_3$) by Kumada Coupling

Step 1: Preparation of MgBrMIP

A dry flask was purged with argon and charged with THF (150 mL), Mg powder (2.5 g, 100 mmol), a few crystals of iodine and 1,2 dibromoethane (1 mL). The mixture was sonicated until the disappearance of iodine color and then a solution of BrMIP (12.40 g, 50 mmol) in THF (50 mL) was added dropwise. The resulting mixture was sonicated until the reaction was complete (judged by HPLC analysis after 1 hour). The excess of magnesium was removed by filtration and the resulting solution of MgBrMIP (0.25 M) was used as such in further transformations.

Step 2: 1-chloro-2-methoxymethyl-4-(trifluoromethyl)benzene

A mixture of (2-chloro-5-(trifluoromethyl)phenyl)methanol (COK) (11.55 g, 55 mmol), NaOH (8.00 g, 200 mmol) and dimethyl sulfate (6.25 mL, 65 mmol) in THF (100 mL) was stired for 5 hours at room temperature. The reaction was quenched with water (20 mL) and 25% ammonia (5 mL) and the resulting mixture was stirred overnight at room temperature. The mixture was purred into water (100 mL) and extracted with petroleum ether (100 mL). The organic phase was washed with 1 M NaOH (aq) (100 mL), water (3×100 mL), brine (50 mL), dried over $Na_2SO_4$ and filtered. The solvent was removed under reduced pressure to yield 1-chloro-2-(methoxymethyl)-4-(trifluoromethyl)benzene (COMK) as a colorless oil (11.54 g, 94%): $^1$H NMR (CDCl$_3$) 3.50 (s, 3H), 4.57 (s, 2H), 7.46 (m, 2H), 7.77 (s, 1H).

Step 3: Kumada Coupling

A dry vial was purged with argon and charged with COMK (215 mg, 1 mmol), Pd(PCy$_3$)$_2$ (1 mol %) and THF (0.5 mL). The mixture was heated for 15 min at 60° C. and a solution of BrMgMIP in THF (~0.25M, 4 mL) was added. The resulting mixture was then heated in microwave oven for 3 hours at 80° C. The reaction mixture was cooled to rt and 2 M HCl (aq) (3 mL) was added. The resulting mixture was extracted with DIPE (3 mL) and the organic layer was washed with water (2×3 mL) and brine (3 mL), dried over $Na_2SO_4$ and filtered. The solvent was removed under reduced pressure to give yellow oil which was purified by flash chromatography to yield 4-fluoro-5-isopropyl-2-methoxy-2'-(methoxymethyl)-4'-(trifluoromethyl)biphenyl (BFOM) as a colorless oil (107 mg, 30%): $^1$H NMR (CDCl$_3$) δ 1.24 (d, J=6.9, 6H), 3.21 (sept., J=6.9, 1H), 3.30 (s, 3H), 3.71 (s, 3H), 4.25 (d, J=32.1, 2H), 6.66 (d, J=12.1, 1H), 7.01 (d, J=8.7, 1H), 7.30 (d, J=8.0, 1H), 7.56 (dd, J=8.0, 1.3, 1H), 7.82 (d, J=0.6, 1H).

Step 4: 2'-(bromomethyl)-4-fluoro-5-isopropyl-2-methoxy-4'-(trifluoromethyl)biphenyl (compound of formula XII'', $R_6$'=—$CH_2Br$)

A mixture of BFOM (356 mg, 1 mmol), acetic acid (2 mL) and 62% HBr (aq) (0.30 mL, 4 mmol) was heated in microwave oven for 15 min at 90° C. The reaction mixture was diluted with water (25 mL), and extracted with petroleum ether (25 mL). The organic phase was washed with water (25 mL), saturated NaHCO$_3$ (aq) (25 mL), water (25 mL), dried over $Na_2SO_4$ and filtered. The solvent was removed under reduced pressure to give slightly yellow oil which was purified by flash chromatography to yield 2'-(bromomethyl)-4-fluoro-5-isopropyl-2-methoxy-4'-(trifluoromethyl)biphenyl (BFBr) as a colorless oil (348 mg, 86%): $^1$H NMR (CDCl$_3$) δ 1.26 (d, J=6.9, 6H), 3.23 (sept., J=6.9, 1H), 3.72 (s, 3H), 4.33 (dd, J=38.2, 9.5, 2H), 6.68 (d, J=12.0, 1H), 7.11 (d, J=8.6, 1H), 7.31 (d, J=8.0, 1H), 7.57 (dd, J=8.0, 1.2, 1H), 7.79 (d, J=1.2, 1 H).

According to the related process 2'-(chloromethyl)-4-fluoro-5-isopropyl-2-methoxy-4'-(trifluoromethyl)biphenyl (compound of formula XII''', $R_6$'=—$CH_2Cl$) using 37% HCl instead of 62% HBr was prepared.

Example 10

Preparation of Anacetrapib (Compound of Formula ACP)

(4'-fluoro-5'-isopropyl-2'-methoxy-4-(trifluoromethyl)biphenyl-2-yl)methanol (compound of formula XII', $R_6$=$CH_2OH$), prepared according to Example 7 is further converted to anacetrapib according to step 6 and 7 of Comparative example 1.

Alternatively, anacetrapib is prepared from 2'-(bromomethyl)-4-fluoro-5-isopropyl-2-methoxy-4'-(trifluoromethyl) biphenyl (compound of formula XII''', $R_6$'=—$CH_2Br$), prepared in Example 8, following step 7 of Example 1.

The intermediate BFCl is substantially free of desmethyl impurities and the final product anacetrapib (compound of formula ACP) is highly pure in view of desmethyl impurities, analysed by HPLC and NMR using identification standard prepared according to Example 1.

The invention claimed is:

1. A process for preparing a compound of formula II

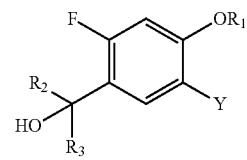

II wherein $R_1$, $R_2$ and $R_3$ are independently from each other selected from substituted or unsubstituted $C_1$-$C_6$ alkyl, and Y is Br, Cl, I or H, which process comprises treating a compound of formula I

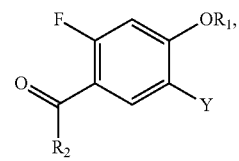

I wherein $R_1$, $R_2$ and Y are defined as above,
with a Grignard reagent in a first solvent, in the presence of a second solvent inert to Grignard reagents selected from the group consisting of $C_1$-$C_6$ haloalkanes, substituted or unsubstituted $C_6$-aromatics and dialkyloxyethanes comprising $C_1$-$C_6$ alkyl moiety/moieties.

2. The process according claim 1, characterized by either one or a combination of the following features a) to f):

a) the reaction is carried out in a mixture of a first solvent and a second solvent wherein the second solvent is inert to Grignard reagents, and is selected from the group consisting of $C_1$-$C_6$ haloalkanes, substituted or unsubstituted $C_6$-aromatics and dialkyloxyethanes comprising $C_1$-$C_6$ alkyl moiety/moieties, or from the group consisting of dichloromethane (DCM), toluene and 1,2-dimethoxyethane (DME);

b) in compound of formula I and II, $R_1$ and $R_3$ are independently from each other selected from substituted or unsubstituted $C_1$-$C_6$ alkyl and wherein $R_2$ is substituted or unsubstituted $C_1$-$C_6$ alkyl wherein $C_1$ has at least one-hydrogen and Y is Br or H, preferably $R_1$, $R_2$ (and $R_3$) are methyl (Me) and Y is H;

the Grignard reagent is $R_3MgX$ wherein $R_3$ is $C_1$-$C_6$ alkyl and X is Cl or Br or I or $R_3MGX$ is MeMgCl;

c) the first solvent is an ether comprising $C_1$-$C_6$ alkyl moiety/moieties and/or phenyl moiety, or the first solvent is selected from the group consisting of diethyl ether, dibutyl ether, methyl tert-butyl ether, anisole, tetrahydrofuran (THF), 1,4-dioxane, or the first solvent is selected from the group consisting of diethyl ether, methyl tert-butyl ether, THF, 1,4-dioxane or the first solvent is THF;

d) the Grignard reagent is used in an amount of 1.0 to 2.0 equivalent(s) relative to compound of formula I, or the amount used is 1.2 to 1.6 equivalent(s);

e) treatment with Grignard reagent is carried out at a temperature below 30° C., or below 5° C., or below 0° C.;

f) compound of formula II comprises an impurity in form of unconverted starting material of compound of formula I in an amount of less than 0.50% by weight relative to the total amount of compound of formula II, or less than 0.25%, or less than 0.15%.

3. The process according to claim 1, wherein the obtained compound of formula II comprises a byproduct in form of compound of formula $III_1$

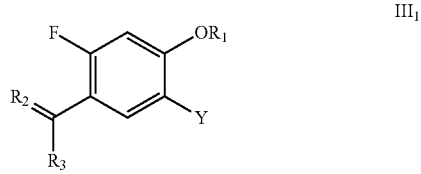

and/or of compound of formula $III_2$

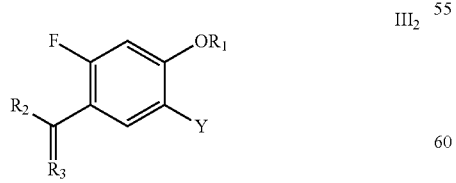

wherein $R_1$ is substituted or unsubstituted $C_1$-$C_6$ alkyl, $R_2$ and $R_3$ are independently from each other selected from substituted or unsubstituted $C_1$-$C_6$ alkyl and alkylidene, and Y is Br, Cl, I or H.

4. The process according to claim 1 wherein a compound of formula II

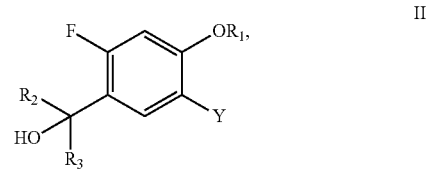

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Y is Br, Cl, I or H, is converted to a compound of formula IV

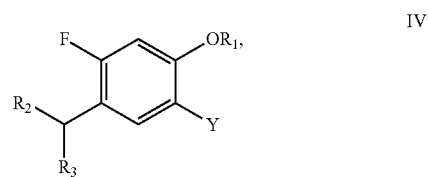

wherein $R_1$, $R_2$, $R_3$ and Y are defined as above, by hydrogenation in the presence of a hydrogenation catalyst;

wherein optionally in this process it is further provided for simultaneous hydrogenation of a byproduct in form of compound of formula $III_1$

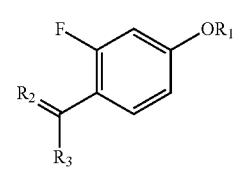

and/or compound of formula $III_2$

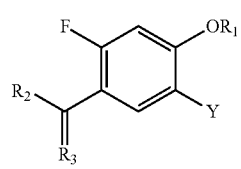

wherein $R_1$ is substituted or unsubstituted $C_1$-$C_6$ alkyl, $R_2$ and $R_3$ are independently from each other selected from substituted or unsubstituted $C_1$-$C_6$ alkyl and alkylidene and Y is Br, Cl, I or H;

and optionally, in a subsequent halogenation step, compound of formula IV'

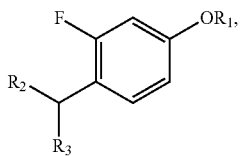

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, is converted to a compound of formula VI

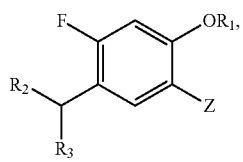

wherein $R_1$, $R_2$ and $R_3$ are defined as above and Z is Br, Cl or I, by treating compound of formula IV' with a halogenating agent.

5. The process according to claim 4, characterized by either one or a combination of the following features i) to v):
   i) compounds of formula III$_1$/III$_2$ are present in an amount of at least 30% by weight relative to the total amount of starting material II or II', or at least 40% by weight, or at least 50% by weight;
   ii) hydrogenation catalyst is removed from the reaction mixture before subsequent treatment with a halogenating agent optionally wherein the catalyst is removed by filtration;
   iii) hydrogenation is carried out in $C_1$-$C_6$ alcohols or $C_1$-$C_6$ alkyl esters of $C_1$-$C_6$ carboxylic acids as the solvent, preferably $C_1$-$C_3$ alcohols or $C_1$-$C_3$ alkyl esters of $C_1$-$C_3$ carboxylic acids, or wherein the solvent is selected from the group consisting of methanol, ethanol, isopropyl alcohol, ethyl acetate, isopropyl acetate and acetic acid, or wherein the solvent is methanol;
   iv) hydrogenation catalyst is selected from the group consisting of palladium-, platinum- or nickel-catalyst, or palladium catalyst, or palladium supported on a solid, or palladium on activated charcoal;
      hydrogenation is carried out using palladium, or palladium supported on a solid, or palladium on activated charcoal, as the catalyst;
   v) halogenation step is carried out using halogenating agents, which are N-halo substituted compounds, or 1,3-dibromo-5,5-dimethylhydantoin (DBDMH).

6. The process according to claim 4, wherein a compound of formula IV or compound of formula VI

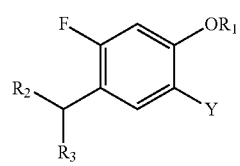

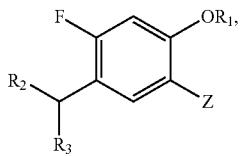

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, Y is Cl, Br, I or H, and Z is Cl, Br or I, is treated with magnesium or zinc, or first with butyllithium, Grignard reagent, magnesium or lithium and followed by $ZnX_2$, wherein X is Cl, Br or I to form a compound of formula VIII

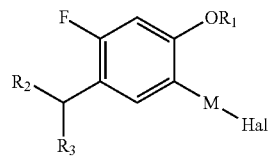

wherein $R_1$, $R_2$ and $R_3$ are defined as above, M is magnesium (Mg) or zinc (Zn), wherein Hal is Cl, Br or I and wherein the compound of formula VIII is subjected to further synthesis steps to yield compound of formula XVI

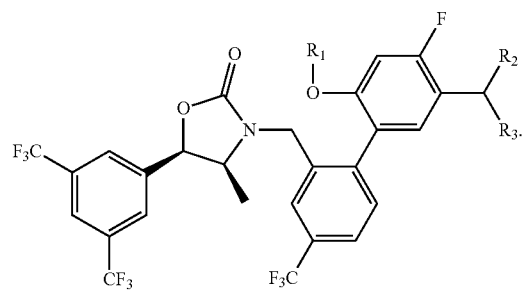

7. The process according to claim 6, wherein compound of formula VIII is treated with trialkyl borate in order to convert compound of formula VIII to a compound of formula IX

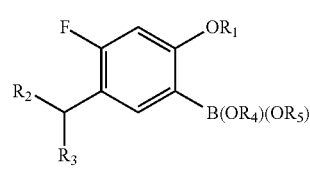

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom and $R_4$ and $R_5$ are selected from H or substituted or unsubstituted $C_1$-$C_6$ alkyl, or $R_4$ or $R_5$ together form a $C_2$-$C_4$ alkylene, or wherein $R_4$ and $R_5$ is H.

8. The process according to claim 7, wherein the compound of formula VIII or the compound of formula IX

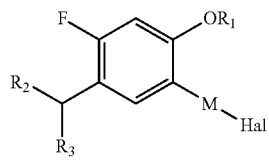

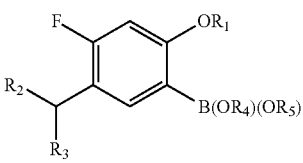

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and $R_4$ and $R_5$ are selected from H or substituted or unsubstituted $C_1$-$C_6$ alkyl, or $R_4$ and $R_5$ together form a $C_2$-$C_4$ alkylene, or wherein $R_4$ and $R_5$ is H, and M is magnesium (Mg) or zinc (Zn), and Hal is selected from Cl, Br or I, is coupled with compound of formula XI

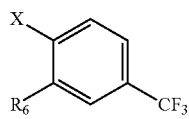

wherein $R_6$ is $CH_2Q$ or a group which can be converted to $CH_2Q$, wherein Q is selected from halogen, hydroxy, acyl or sulfonyl substituted hydroxy, amino, acyl or sulfonyl substituted amino, or wherein $R_6$ is selected from the group consisting of hydroxymethyl, alkoxymethyl, halomethyl, carboxy, alkoxycarbonyl, amidocarbonyl, cyano, formyl, 2-(4,5-dihydro-1,3-oxazolyl) and X is Cl, Br or I to form a compound of formula XII,

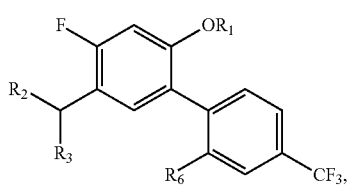

wherein $R_1$, $R_2$, $R_3$ and $R_6$ are defined as above, in the presence of a catalyst.

9. The process according to claim 4, wherein the compound of formula VI

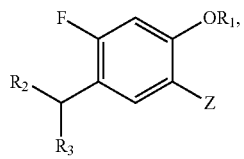

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Z is Cl, Br or I, is treated with a compound of formula XIII

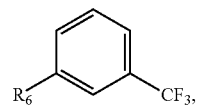

wherein $R_6$ is carboxy or carboxamide carboxyamide group in the presence of a coupling catalyst to form a compound of formula XII,

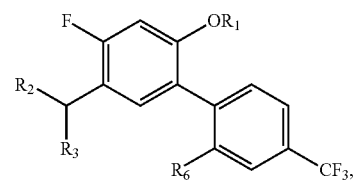

wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and $R_6$ is carboxy or carboxyamide group.

10. The process according to claim 9, characterized by either one or a combination of the following features (a) to (c):
  (a) polar aprotic solvent is present in the reaction mixture;
  (b) the reaction mixture is heated above 20° C.;
  (c) the coupling catalyst is selected from the group consisting of palladium-triarylphosphine, trialkylphosphine complex with palladium in the zero oxidation state, salt of palladium in the presence of triarylphosphine and trialkylphosphine as a complex ligand, and metallic palladium optionally supported on a solid in a suitable solvent.

11. The process according to claim 1, wherein a compound of formula II

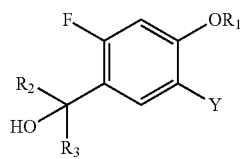

is provided in which $R_1$, $R_2$ and $R_3$ are methyl and Y is Br, Cl, I or H, the process further comprising the steps of:
a) converting the compound of formula II to a compound of formula IV

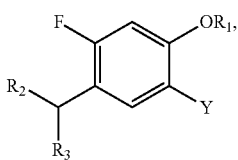

IV wherein $R_1$, $R_2$, $R_3$ and Y are defined as above,
by hydrogenation in the presence of a hydrogenation catalyst;
b) treating the compound of formula IV with magnesium or zinc, or first with butyllithium, Grignard reagent, magnesium or lithium and followed by $ZnX_2$, wherein X is Cl, Br or I to form a compound of formula VIII

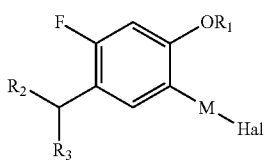

VIII wherein $R_1$, $R_2$, and $R_3$ are defined as above, M is magnesium (Mg) or zinc (Zn), and wherein Hal is Cl, Br or I;
c) treating the compound of formula VIII with trialkyl borate to form a compound of formula IX

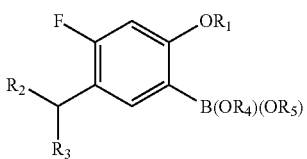

IX wherein $R_1$, $R_2$, and $R_3$ are defined as above, and $R_4$ and $R_5$ are selected from H or substituted or unsubstituted $C_1$-$C_6$ alkyl, or $R_4$ and $R_5$ together form a $C_2$-$C_4$ alkylene, or wherein $R_4$ and $R_5$ are H;
d) coupling the compound of formula VIII or formula IX with a compound of formula XI

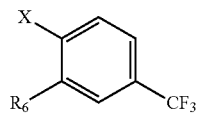

XI wherein $R_6$ is $CH_2Q$ or a group which can be converted to $CH_2Q$, wherein Q is selected from halogen, hydroxy, acyl or sulfonyl substituted hydroxy, amino, acyl or sulfonyl substituted amino, or wherein $R_6$ is selected from the group consisting of hydroxymethyl, alkoxymethyl, halomethyl, carboxy, alkoxycarbonyl, amidocarbonyl, cyano, formyl, 2-(4,5-dihydro-1,3-oxazolyl) and X is Cl, Br or I to form a compound of formula XII,

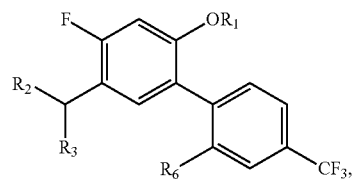

XII wherein $R_1$, $R_2$, $R_3$ and $R_6$ are defined as above,
in the presence of a catalyst;
e) coupling the compound of formula XII with a compound of formula XVII

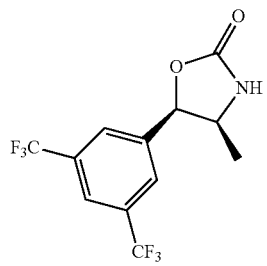

XVII in the presence of a base to yield anacetrapib.

12. The process according to claim 4, wherein compound of formula II

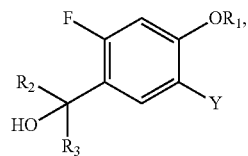

II wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, and Y is H, is converted to a compound of formula VI

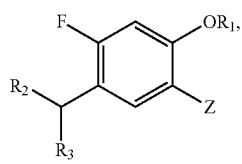

VI wherein $R_1$, $R_2$, $R_3$ are defined as above, and Z is Br, Cl or I,
in the presence of hydrogen and a hydrogenation catalyst and subsequent halogenation step by treating the reaction mixture with a halogenating agent in a one-pot reaction process.

13. The process according to claim 4, wherein compound of formula IV or compound of formula VI

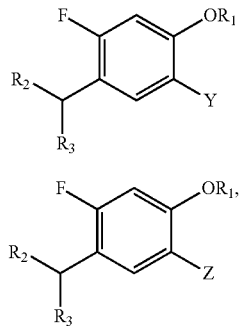

IV

VI wherein $R_1$ and $R_3$ are independently from each other selected from substituted or unsubstituted $C_1$-$C_6$ alkyl and $R_2$ is substituted or unsubstituted $C_1$-$C_6$ alkyl wherein $C_1$ has at least one hydrogen atom, Y is Cl, Br, I or H, and Z is Cl, Br or I, contain less than 4% by weight of compound of formula VII relative to the total amount of compound of formula IV or VI

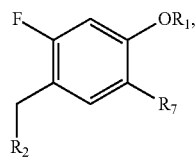

VII wherein $R_1$ is substituted or unsubstituted $C_1$-$C_6$ alkyl and $R_2$ is substituted or unsubstituted $C_1$-$C_6$ alkyl wherein $C_1$ has at least one hydrogen atom, and $R_7$ is selected from the group consisting of H, Cl, Br, I group.

14. The process according to claim 1, wherein a compound of formula XVI is produced

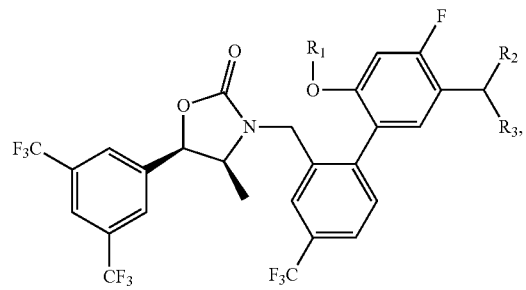

XVI wherein $R_1$ and $R_3$ is substituted or unsubstituted $C_1$-$C_6$ alkyl and $R_2$ is substituted or unsubstituted $C_1$-$C_6$ alkyl wherein $C_1$ has at least one hydrogen atom, and wherein a compound of formula XV

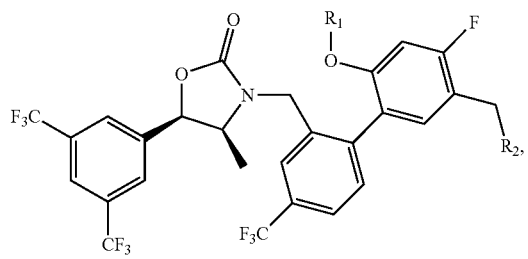

XV wherein $R_1$ is substituted or unsubstituted $C_1$-$C_6$ alkyl and $R_2$ is substituted or unsubstituted $C_1$-$C_6$ alkyl wherein $C_1$ has at least one hydrogen atom, or $R_1$ and $R_2$ is methyl, is present as in impurity in the compound of formula XVI in an amount less than 0.20% by weight relative to the total amount of compound of formula XVI.

* * * * *